US006472175B1

(12) United States Patent
Wood

(10) Patent No.: US 6,472,175 B1
(45) Date of Patent: Oct. 29, 2002

(54) SIALYLATION OF N-LINKED GLYCOPROTEINS IN THE BACULOVIRUS EXPRESSION VECTOR SYSTEM

(75) Inventor: H. Alan Wood, Ithaca, NY (US)

(73) Assignee: Boyce Thompson Institute For Plant Research, Inc., Ithaca, NY (US)

( * ) Notice: Subject to any disclaimer, the term of this patent is extended or adjusted under 35 U.S.C. 154(b) by 0 days.

(21) Appl. No.: 09/714,085

(22) Filed: Nov. 17, 2000

Related U.S. Application Data

(63) Continuation-in-part of application No. 09/353,897, filed on Jul. 15, 1999, now Pat. No. 6,261,805.

(51) Int. Cl.[7] .............................. C12Q 1/68; C12Q 1/70; C12N 15/866; C12N 5/10

(52) U.S. Cl. .............................. 435/69.1; 435/5; 435/6; 435/325; 435/348; 435/320.1

(58) Field of Search ........................... 435/69.1, 320.1, 435/325, 348, 5, 6; 530/350

(56) References Cited

U.S. PATENT DOCUMENTS 5,153,131 A  10/1992  Wolf et al.
5,362,490 A  11/1994  Kurimoto

OTHER PUBLICATIONS

Verne A. Luckow, Protein Production and Processing from Baculovirus Expression Vectors, pp 15–18, 1993.*
Altmann, F., Kornfeld, G., Dalik, T., Staudacher, E., &Glossl, J., (1993), Processing of asparagine–linked oligosaccharides in insect cells—N–acetylglucosaminyltransferase I and II activities in cultured lepidopteran cells, Glycobiology 3: 619–625.
Altmann, F., & Marz, L., (1995), Processing of asparagine–linked oligosaccharides in insect cells—evidence for alpha–mannosidase–II, Glycoconjugate Journal, 12: 150–155.
Baenziger, J.U. (1985), The role of glycosylation in protein recognition, Amer. J. Path. 121:382–391.
Bechler, B., Cogoli, A., Cogoli–Greuter, M., Mueller, O., Hunzinger,E. and Criswell, S. B. (1992), Activation of microcarrier–attached lymphocytes in microgravity, Biotechnol. Bioengin. 40:991–996.
Ben–Zeev, A. (1990), Application of two–dimensional gel electrophoresis in the study of cytoskeletal protein regulation during growth activation and differentiation, Electrophoresis 11:191–200.
Botteri, F.M., Ballmer–Hofer, K., Rajput, B. and Nagamine, Y.(1990), Disruption of cytoskeletal structures results in the induction of the urokinase–type plasminogen activator gene expression, J. Biol.Chem. 165:13327–13334.

Chalmers, J. J. (1995), The effect of hydrodynamic forces on insect cells. In: Baculovirus Expression Systems and Biopesticides (M.L. Shuler, H.A. Wood, R.R. Granados, and D.A. Hammer, eds.), Wiley, NY., 175–204.
Chazenbalk, G. and Rapoport, B. (1995), Expression of the extracellular domain of the thyrotropin receptor in the baculovirus system using a promoter active earlier than the polyhedrin promoter, Journal of Biological Chemistry 27: 1543–1549.
Cherry, R.S. and Hulle, C.T. (1992), Cell death in the thin films of bursting bubbles, Biotechnol. Prog. 8:11–18.
Davidson, D.J. and Castellino, F.J. (1991), Structures of the asparagine–289–linked oligosaccharides assembled on recombinant human plasminogen expressed in a *Mamestra brassicae* cell line (IZD–MB0503), Biochemistry 30:6689–6696.
Davis, T.R. and Wood, H.A. (1995), Intrinsic glycosylation potentials of insect cell cultures and insect larvae. In Vitro Cellular and Development Biology 31:659–663.
Davis, T.R., Trotter, K.M., Granados, R.R. and Wood, H.A. (1992), Baculovirus expression of alkaline phosphatase as a reporter gene for evaluation of production, glycosylation and secretion, Bio/Technology 10:1148–1150.
Davis, T.R., Wickham, T.J., McKenna, K.A., Granados, R.R., Shuler M.L.and Wood, H.A. (1993a), Comparative recombinant protein production of eight insect cell lines, In Vitro Cell. Dev. Biol. 29A: 388–390.
Davis, T.R., Shuler, M.L., Granados, R.R. and Wood, H.A. (1993b),Comparison of oligosaccharide processing among various insect celllines expressing a secreted glycoprotein, In Vitro Cell. Dev. Biol 29A: 842–846.
Domingo, D.L. and Trowbridge, I.S. (1988), Characterization of the human transferrin receptor produced in a baculovirus expression system, J. Biol. Chem. 263:13386–13392.
Feizi, T. and Childs, R.A. (1987) Carbohydrates as antigenic determinants of glycoproteins, Biochem. J. 245:1–11.
Francis, K.M., O'Connor, K., and Spaulding, G.F. (1997), Cultivation of fall army worm ovary cells in simulated microgravity. In Vitro CellDev. Biol. 33: 332–336.
Fuchs, B.B. and Medvedev, A.E. (1993), Countermeasures for ameliorating in–flight immune dysfunction. J. Leukocyte Biol. 54:245–252.

(List continued on next page.)

Primary Examiner—David Guzo
(74) *Attorney, Agent, or Firm*—Brown & Michaels, PC

(57) ABSTRACT

The present disclosure utilizes a novel approach to protein preparation in the baculovirus expression vector system (BEVS). Specifically, the present invention analyzes the effects of supplementing insect cell culture media with dexamethasone or N-acetylmannosarnine on complex glycosylation of proteins prepared via BEVS, including the addition of terminal sialic acid residues to N-linked oligosaccharides.

13 Claims, 6 Drawing Sheets

OTHER PUBLICATIONS

Gavrilova, O.V., Gabova, A.V., Goryainova, L.N., and Filatova, E.V.(1992), Experiment with *Chlamydomonas reinhardtii* on board Cosmos–2044 biosatellite, Aviakosm Ekolog Med. 26:27–30.

Glacken, M.W., Fleischaker, R.J. and Sinskey, A.J. (1983), Mammalian cell culture: Engineering principles and scale–up, Trends Biotechnol. 1:4.

Goochee, C.F. and Monica, T. (1990), Environmental effects on protein glycosylation, Bio/Tech. 8:421–427.

Greenfield, C., Patel, G., Clark, S., Jones, N. and Waterfield, M.D.(1988), Expression of the human EGF receptor with ligand–stimulatable kinase activity in insect cells using a baculovirus vector, EMBO J.7:139–146.

Guile, G. R., Rudd Pauline, M., Wing David, R., Prime Sally,B., & Dwek Raymond, A., (1996), A rapid high–resolution high–performance liquid chromatographic method for separating glycan mixtures and analyzing oligosaccharide profiles, Analytical Biochemistry 240: 210–226.

Hilaire, E., Paulsen, A.Q., Brown, C.S., and Guikema, J.A. (1995), Effects on clinorotation and microgravity on sweet clover columella cells treated with cytochalasin D, Physiologia Plantarum 95:267–273.

Hollister, J. R., Shaper, J. H., & Jarvis, D. L., (1998), Stable Expression of mammalian beta 1,4–galactosyltransferase extends the N–glycosylation pathway in insect cells, Glycobiology 8: 473–480.

Hooker, A.D., Goldman, M.H., Markham, N.H., James, D.C., Ison, A.P., Bull, A.T., Strange, P.G., Salmon, I., Baines, A.J., and Jenkins, N. (1995), N–Glycans of recombinant human interferon Ñ change during batch culture of Chinese Hamster Ovary cells, Biotechnol. Bioeng. 48: 639.

Hsu, T. A., Takahashi, N., Tsukamoto, Y., Kato, K., Shimada, I., Masuda, K., Whiteley, E. M., Fan, J. Q., Lee, Y. C., & Betenbaugh, M.J., (1997), Differential N–glycan patterns of secreted and intracellular IgG produced in Trichoplusia ni cells, Journal of Biological Chemistry 272:9062–9070.

Hymer, W.C., Slada, T., Avery, L. and Grindeland, R.E. (1996), Experimental modification of rat pituitary prolactin cell function during and after spaceflight, J. Appl. Physiol. 80:971–980.

Jarvis, D. L., & Finn, E. E., (1996), Modifying the insect cell N–glycosylation pathway with immediate early baculovirus expression vectors, Nature Biotechnology 14: 1288–1292.

Jarvis, D. L., Kawar, Z. S., & Hollister, J. R., (1998), Engineering N–glycosylation pathways in the baculovirus–insect cell system, Current Opinion in Biotechnology 9: 528–533.

Junker, B.H., Wu, F., Wang, S., Waterbury, J., Hunt, G., Hennessey,J., Aunins, J.,Lewis, J., Silberklang, M., and Buckland, B. C. (1992), Evaluation of a microcarrier process for large–scale cultivation of attenuated hepatitis A, Cytotechnology 9:173–187.

Kretzschmar, E., Geyer, R., & Klenk, H. D., (1994), Baculovirus infection does not alter N–glycosylation in *Spodoptera frugiperda* cells, Biological Chemistry Hoppe Seyler 375:323–327.

Kubelka, V., Altmann, F., Kornfeld, G., & Marz, L., (1994), Structures of the N–linked oligosaccharides of the membrane– glycoproteinsfrom 3 lepidopteran cell–lines (Sf–21, Izd–Mb– 0503, Bm–N), Archives of Biochemistry and Biophysics 308: 148–157.

Kuroda, L., Geyer, H., Geyer, R., Doerfler, W., & Klenk, H.–D., (1990), The oligosaccharides of influenza virus hemagglutinin expressed in insect cells by a baculovirus vector, Virology 174: 418–429.

Mattu, T. S., Pleass, R. J., Willis, A. C., Kilian, M., Wormald, M. R., Lellouch, A. C., Rudd, P. M., Woof, J. M., & Dwek, R. A., (1988), The glycosylation and structure of human serum IgA1, Fab, and Fcregions and the role of N–glycosylation on Fc receptor interactions, Journal of Biological Chemistry 273: 2260–72.

McKenna, M.J., Hamilton, T.A. and Sussman, H.H. (1979), Comparison of human alkaline phosphatase isoenzymes, Biochem. J. 181:67–73.

McFarlane, I.G. (1983), Hepatic clearance of serum glycoproteins, ClinSci. 64:127–135.

Moore, R., McClelen, C.E., Fondren, W.M. and Wang, C.L. (1987), Influence of microgravity on root–cap regeneration and structure of columella cells in *Zea–mays*, Am. J. Bot. 74:218–223.

Murhammer, D.W. and Goochee, C.F. (1990), Sparged animal cell bioreactors: mechanism of cell damage and Pluronic F–68 protection, Biotechnol. Prog. 6:391–397.

O'Connor, K., Prewett, T., Goodwin, T., Francis, K., Andrews, A.and Spaulding, G. (1993), Application of simulated microgravity to mammalian and insect cell cultivation: a study with the NASA rotating–wall vessel, 1993 Meeting of the Am. Inst. of Chem.Engineers, St. Louis, MO, Nov. 7–12. Extended Abstracts p. 250.

O'Connor, K.C., Prewett, T.L., Goodwin, T.J., Francis, K.M.,Andrews, A.D. and Spaulding, G.F. (1994), Animal–cell cultivation in the NASArotating–wall vessel. In: Animal Cell Technology: Products for Today, Prospects for Tomorrow (R.E. Spier, J.B. Griffiths and W. Berthold, eds.), Butterworth–Heinemann. London. pp. 293–295.

Ogonah, O. W., Freedman, R. B., Jenkins, N., Patel, K., &Rooney, B. C., (1996), Isolation and characterization of an insect cell line able to perform complex N–linked glycosylation on recombinant proteins, Bio–Technology 14: 197–202.

Ren, J. X., Castellino, F. J., & Bretthauer, R. K., (1997), Purification and properties of alpha–mannosidase II from Golgi– like membranes of baculovirus–infected *Spodoptera frugiperda* (IPLB–SF–21AE) cells, Biochemical Journal 324: 951–956.

Rennison, M.E., Handel, S.E., Wilds, C.J. and Burgoyne, R.D. (1992), Investigation of the role of microtubules in protein secretion from lactating mouse mammary epithelial cells, J. Cell Sci 102:239–247.

Roth et al. (1992), Occurrence of Sialic Acids in *Drosophila melanogaster*, Science 256: 673–675.

Schauer, R. (1988), Sialic acids as antigenic determinants of complexcarbohydrates, Adv. Exp. Med. Biol. 228:47–72.

Shuler, M.L., Cho, R., Wickham, T., Ogonah, O., Kool, M., Hammer,D.A., Granados, R.R. and Wood, H.A. (1990), Bioreactor development for production of viral pesticides or heterologous proteins in insect cell cultures. Ann. N. Y. Acad. Sci. 589:399–422.

Spaulding, G.F., Jessup, J.M. and Goodwin, T.J. (1993), Advances in cellular construction, J. Cell. Biochem. 51:249–251.

Staudacher, E., Altmann, F., Marz, L., Hard, K., Kamerling, J.P., & Vliegenthart, J. F. G., (1992), Alpha–1–6 (Alpha–1–3)–difucosylation of the asparagine–bound N–acetylglucosamine in honeybee venomphospholipase–A2, Glyconjugate Journal 9: 82–85.

Taticek, R.A., Hammer, D.A. And Shuler, M.L. (1995), Overview of issues in bioreactor design and scale–up. In: Baculovirus Expression Systems and Biopesticides (M.L. Shuler, H.A. Wood, R.R. Granados, and D.A.Hammer, eds.), Wiley, N.Y., 131–174.

Tramper, J. and Vlak, J. (1986), Some engineering and economic apsects of continuous cultivation of insect cells for the production of baculoviruses, Annals N.Y. Acad. Sci. 469:279–288, 1986.

van Die, I., van Tetering, A., Bakker, H., van denEijnden, D.H., & Joziasse, D. H., (1996), Glycosylation in Lepidopteran insect cells: Identification of a beta 1–>4–N–acetylgalactosaminyltransferase involved in the synthesis of complex–type oligosaccharide chains, Glycobiology 6: 157–164.

Vialard, J., Lalumiere, M., Vernet, T., Briedis, D., Alkhatib, G.,Henning, D., Levin, D. and Richardson, C. (1990), Synthesis of the membrane fusion and hemagglutinin proteins of measles virus, using a novelbaculovirus vector containing the §–galactosidase gene, J. Virol. 64:37–50.

Vissavajjhela, P. and Ross, A.H. (1990), Purification and characterization of the recombinant extracellular domain of human nerve growth factor receptor expressed in a baculovirus system, J.Biol. Chem. 265:4746–4752.

Wagner, R., Geyer, H., Geyer, R., & Klenk, H. D., (1996a), N–acetyl–beta–glucosaminidase accounts for differences in glycosylation of influenza virus hemagglutinin expressed in insect cells from a baculovirus vector, Journal of Virology 70:4103–4109.

Wanger, R., Liedtke, S., Kretzschmar, E., Geyer, H., Geyer, R., & Klenk, H. D., (1996b), Elongation of the N–glycans of fowl plaguevirus hemagglutinin expressed in *Spodoptera frugiperda* (Sf9) cells by coexpression of human beta–1,2 N–acetylglucosaminyltransferase I, Glycobiology 6: 165–175.

Wathen, M. W., Brideau, R. J., & Thomsen, D. R., (1989), Immunization of cotton rats with the human respiratory syncytial virus glycoprotein produced using a baculovirus vector, J Infect Dis 159:255–264.

Weiss, S.A., Orr, T., Smith, G.C., Kalter, S.S., Vaughn, J.L. andDoughtery, E.M. (1982), Quantitative measurement of oxygen consumption in insect cell culture infected with polyhedrosis virus. Biotechnol.Bioeng, 24:1145–1154.

Welply, J.K. (1991), Protein glycosylation: function and factors that regulate oligosaccharide structure. In Animal Cell Bioreactors (C.S. Ho and D.I.C. Wang, eds.) Butterworth–Heinemann, Boston.

Wickham, T.J., Davis, T., Granados, R.R., Shuler, M.L. and Wood, H.A.(1992),Screening of insect cell lines for the production of recombinant proteins and infectious virus in the baculovirus expression system, Biotechno. Prog. 8:391–396.

Wu, D.S., Gao, X.Y., Chen, Y.S., Li, R.Q., and Guo, Y.S. (1994), Adaptive responses of leaf cells of rice seedlings to horizontal clinostatic conditions, Acta Botanica Sinica 36:364–369.

Davidson et al. (1991), Oligosaccharide Processing in the Expression of Human Plasminogen cDNA by Lepidopteran Insect (*Spodoptera frugiperda*) cells, Biochemistry 29: 5584–5590.

Russo et al. (1998), Expression of bovine leukemia virus ENV glycoprotein in insect cells by recombinant baculovirus. FEBS Letters 436: 11–16.

Sridhar et al. (1993), Temporal nature of the promoter and not relative strength determines the expression of an extensively processed protein in a baculovirus system, FEBS 315(3): 282–286.

Kato et al. (1994), Haemagglutination activity of haemolymph of Bombyx mori treated with a juvenile hormone analogue, J. Seric. Sci. Jpn. 63(3): 221–228.

Vandenbroeck et al. (1994), Glycoform Heterogeneity of Porcine Interferon–$\gamma$ Expressed in Sf9 Cells, Lymphokine and Cytokine Research 13(4): 253–258.

Donaldson et al. (1999), Glycosylation of a recombinant protein in the Tn5b1–4 insect cell line: influence of ammonia, time of harvest, temperature, and dissolved oxygen, Biotechnology and Bioengineering 63(3):255–262.

Kulakosky et al. (1998a), N–Glycosylation of a baculovirus–expressed recombinant glycoprotein in three insect cell lines, In Vitro Cell. Dev. Biol– Animal 34:101–108.

Kulakosky et al. (1998b), N–linked glycosylation of a baculovirus–expressed recombinant glycoprotein in insect larvae and tissue culture cells, Glycobiology 8(7): 741–745.

Prewett et al. (1993), Three–Dimensional Modeling of T–24 Human Bladder Carcinoma Cell Line: A new stimulated microgravity culture vessel, J. Tiss. Cult. Meth. 15:29–36.

NASA Tech Briefs, MSC–22336, Cultivating Insect Cells to Produce Recombinant Proteins.

Kelly, D.C. et al; 1983; Baculovirus Replication: Glycosylation of Polypeptides Synthesized in Trichoplusis ni Nuclear Polyhedrosis Virus–infected Cells and the Effect of Tunicamycin; J. Gen Virology; 64: 1915–1926.

Keppler, O.T. et al, 1999; "UDP–GlcNAc 2–Epimerase: A Regulator of Cell Surface Sialylation"; Science; vol. 284; p. 1372–1376.

* cited by examiner

Sf-9 cells
Serum-containing medium
Flask

BTI-Tn-5B1-4h cells
Serum-containing medium
Flask

BTI-Tn-5B1-4h cells
Serum-free medium
Flask

BTI-Tn-5B1-4h cells
Serum-containing medium
Flask

BTI-Tn-5B1-4h cells
Serum-containing medium
HARV

SIALYLATION OF N-LINKED GLYCOPROTEINS IN THE BACULOVIRUS EXPRESSION VECTOR SYSTEM

REFERENCE TO RELATED APPLICATIONS

This is a continuation in part application of U.S. patent application Ser. No. 09/353,897, filed Jul. 15, 1999, now U.S. Pat. No. 6,261,305, entitled "SIALYLATION OF N-LINKED GLYCOPROTEINS IN THE BACULOVIRUS EXPRESSION VECTOR SYSTEM". The aforementioned application is hereby incorporated herein by reference.

ACKNOWLEDGMENT OF GOVERNMENT SUPPORT

The research that led to this invention was partially funded by Government support under Grant No. NAG8-1384, awarded by the National Aeronautical Space Administration. The government has certain rights in the invention.

FIELD OF THE INVENTION

The invention pertains to the field of protein expression systems. More particularly, the invention pertains to optimizing the N-linked glycosylation of proteins in a baculovirus expression system.

BACKGROUND OF THE INVENTION

Glycobiology is a newly emerging area of biotechnology. Most of the extracellular proteins of higher animals are glycoproteins, including proteins of pharmaceutical interest such as erythropoietin, tissue plasminogen, interleukins and interferons. The ubiquity and diversity of glycoproteins is matched by the breadth of functions that they have in a wide range of important biological processes. For instance, glycosylation plays an important role in hormone signal transduction and in the biological activity of immunoglobulins. Glycoproteins also play a structural role in connective tissues such as collagen. Glycosylation of proteins clearly represents one of the most important co- and post-translational events.

Glycoproteins are composed of a polypeptide chain covalently bound to one or more carbohydrate moieties. There are two broad categories of glycoproteins with carbohydrates coupled through either N-glycosidic or O-glycosidic linkages to their constituent protein. The N- and O-linked glycans are attached to polypeptides through asparagine-N-acetyl-D-glucosamine and serine (threonine)-N-acetyl-D-galactosamine linkages, respectively. Complex N-linked oligosaccharides do not contain terminal mannose residues. They contain only terminal N-acetylglucosamine, galactose, and/or sialic acid residues. Hybrid oligosaccharides contain terminal mannose residues as well as terminal N-acetylglucosamine, galactose, and/or sialic acid residues.

With N-linked glycoproteins, an oligosaccharide precursor is attached to the amino group of asparagine during peptide synthesis in the endoplasmic reticulum. The oligosaccharide moiety is then sequentially processed by a series of specific enzymes that delete and add sugar moieties. The processing occurs in the endoplasmic reticulum and continues with passage through the cis-, medial- and trans-Golgi apparatus (FIGS. 1A and B).

The regulation of the glycosylation process is complex because it contains both synthetic and degradative steps that are controlled by very specific enzymes. Currently, the regulation of glycoprotein synthesis and processing is not well understood.

Glycosylation in the Baculovirus Expression System

It has been estimated that the baculovirus-polyhedrin protein can constitute up to 50% of the total protein mass at cell death. The polyhedrin gene is one of the most highly expressed viral genes described. One of the reasons for this high expression level is that the polyhedrin gene is under the transcriptional control of a very strong promoter. Replacement of the polyhedrin gene open-reading-frame (ORF) with the ORF of a foreign gene under the control of the polyhedrin gene promoter results in high levels of expression of the foreign gene product. Production levels as high as 1 mg/$10^6$ cells have been obtained. This method of producing foreign proteins is referred to as the baculovirus expression vector system (BEVS).

Hundreds of proteins have been expressed in stationary insect cell cultures with the baculovirus expression vector system (BEVS). There is substantial pharmaceutical interest in using the BEVS to produce commercial products in insect cells. The BEVS has several advantages as a recombinant protein production system, such as 4–6 weeks from gene isolation to BEVS expression, high production levels and the absence of adventitious viruses (commonly found in mammalian tissue culture cells). Equally important is the fact that insect cells are able to recognize the co- and post-translational signals of higher eukaryotes, resulting in processing such as phosphorylation, proteolytic processing, carboxyl methylation, and glycosylation. Of all these co- and post-translational processing events, glycosylation has been found to have the greatest influence on many of the physical and functional properties of proteins.

Altering the type of glycan modifying a glycoprotein can have dramatic affects on a protein's antigenicity, structural folding, solubility, and in vivo bioactivity and stability. Also, varying the number and composition of the oligosaccharide moieties can significantly alter the physical characteristics for many glycoproteins. In particular, it has been demonstrated that terminal sialic acid residues play an extremely important role in defining the in vivo biological activity of many glycoproteins. For example, terminal sialic acid residues have been demonstrated to be very important in defining the immunogenicity of glycoproteins.

The absence of sialic acid has been found to influence the biological activity of many proteins. In particular, the specific activities of proteins, such as tissue plasminogen (used clinically to dissolve blood clots) and erythropoietin (which stimulates maturation of red blood cells), have been found to be dramatically altered by the removal of terminal sialic acid residues. Furthermore, the specific recognition of oligosaccharide moieties is the primary mechanism for protein clearance from the circulatory system. Therefore, differences in the oligosaccharide structure, particularly the presence or absence of sialic acid, can significantly affect both the in vivo and in vitro properties of glycoproteins. Thus, if insect cells are used to produce therapeutic glycoproteins, it is critical to generate glycoproteins with terminal sialic acid residues.

Experience with the expression of N-linked glycoproteins using the BEVS clearly indicates that insect cells generally recognize the same signals for glycosylation sites as mammalian cells. The N-linked glycosylation pathway is outlined in FIGS. 1A and B. Glycosylation begins with the attachment of the dolichol-phosphate precursor oligosaccharide. Following this initial step, there is efficient removal of glucose residues by α-glucosidase I and II and subsequent removal of mannose residues with endoplasmic reticulum mannosidase and Golgi mannosidase I. This glycan trimming process appears to progress in a proficient fashion in lepidopteran larvae and tissue culture cells.

Following these trimming events, mammalian glycan processing is typically subject to the sequential enzymatic addition of N-acetylglucosamine (GlcNAc), sometimes fucose, followed by galactose (Gal) and sialic acid residues (FIGS. 1A and B). However, mammalian glycoproteins that normally have complex glycans with terminal sialic acid residues when they are produced in mammalian cells, are expressed in the BEVS in insect cells with oligosaccharides containing high mannose ($Man_{8-5}GlcNAc_2$) or paucimannose ($Man_{2-3}GlcNAc_2$) structures (note the absence of sialic acid residues). Some of the structures contain α1,6 linked fucose and/or terminal GlcNAc residues. Note that in the foregoing descriptions of oligosaccharide structures, the term "Man" is an abbreviation used to described mannose.

Early studies of N-linked glycoproteins expressed in the BEVS suggested that insect cells were not able to add GlcNAc, Gal or sialic acid residues (Wathen et al., 1989; Kuroda et al., 1990; Kretzschmar et al., 1994). However, the enzymes required for the addition of GlcNAc and Gal residues have been identified in insect cell lines derived from *B. mori* (Bm-N), *Mamestra brassicae* (IZD-Mb-05030, referred to as Mb) and *Spodoptera frugiperda* (IPLB-SF21AE, referred to as Sf-9 and Sf-21). β1,2-N-acetylglucosaminyltransferase I (GlcNAc-T-I) activity has been found in Bm-N, Mb, Sf-9 and Sf-21 tissue culture cells (Altmann el al., 1993). However, it should be noted that the high level of GlcNAc-T-I activity found in the Bm-N, Mb and Sf-21 tissue culture cells by Altmann et al. (1993) was not reflected in the N-linked oligosaccharide structures associated with cell membranes characterized by Kubelka et al. (1994). Only a small percentage of the membrane-associated structures had terminal GlcNAc residues.

Following the addition of the first GlcNAc residue, typically two additional terminal mannose residues are removed by the action of a Golgi mannosidase II (FIG. 1B). Altmann and März (1995) demonstrated α-D-mannosidase II activity in Bm-N, Sf-21 and Mb insect cell lines. The enzymatic activity appeared to be membrane-bound. Ren et al. (1997) purified this enzyme from Sf-21 cells and found similar properties to those reported by Altmann and März (1995).

The resulting glycans with terminal GlcNAc residues can be fucosylated. Staudacher et al. (1992) found fucosyltransferase activity in Mb cells that transferred fucose to the innermost GlcNAc residue with α1,6 and α1,3 linkages. In addition, they identified fucosyltransferase activity for α1,6 fucosyl linkages in extracts from Bm-N and Sf-9 cells.

Altmann et al. (1993) also investigated the fucosyltransferase activity in Mb tissue culture cells. Based on substrate preference, they concluded that the go-signal for the lepidopteran fucosyltransferase was a GlcNAc residue on the α1,3 arm, the product of the GlcNAc-T-1 activity that they had previously found in these cells. Despite this apparent requirement by fucosyltransferase, Kubelka et al. (1994) found a low percentage of structures with GlcNAc residues on the α1,3 arm, but a high percentage of fucosylated structures.

An explanation for this apparent contradiction is that following addition of GlcNAc to the α1,3 arm and subsequent fucosylation, the terminal GlcNAc residue is removed by β-N-acetylglucosaminidase (GlcNAcase). In contrast, Ogonah et al. (1996) found an abundance of glycan structures with terminal GlcNAc residues attached to human interferon-γ produced in *Estigmene acrea* (Ea-4), but not in Sf-9 tissue culture cells. The reason for this is that *Estigmene acrea* cells contain little or no GlcNAcase activity.

The digestion with a GlcNAcase is consistent with the paucimannose structures attached to secreted alkaline phosphatase during synthesis in five insect larvae and five cell lines (Kulakosky el al., 1998b). It was observed that all larval and cell culture samples except the Sf-21 cell culture samples contained high concentrations of fucosylated and nonfucosylated paucimannose structures that lacked terminal α1,3 mannose. This suggested that, following the removal of the GlcNAc from the α1,3 arm, an α1,3 mannosidase might remove the terminal mannose, leaving a structure that could not be further modified.

However, in the absence of GlcNAcase, an additional GlcNAc residue can be added to the α1,6 arm through the action of β1,2-N-acetylglucosaminyltransferase II (GlcNAc-T-II). Altmann et al. (1993) reported finding low levels of GlcNAc-T-II activity in Bm-N, Mb, Sf-9 and Sf-21 tissue culture cells. Their data indicated that the GlcNAc-T-II was responsible for the addition of a GlcNAc residue β1,2 linked to the α1,6 arm.

The resulting structures would be substrates for the enzymatic addition of Gal residues. A β1,4 galactosyltransferase has been reported in BTI-Tn-5b2-4 (High Five™), Sf-9 and Mb tissue culture cells. This suggests that insect cells have the necessary enzymatic machinery for processing complex glycans containing terminal Gal residues. However, very few recombinant glycoproteins produced in insect cells have been found to have oligosaccharides with terminal Gal residues.

There is considerable interest in producing N-linked glycoproteins that have glycan structures terminating with sialic acid residues. However, the requisite sialyltransferase activity has not been reported in insect cells. This fact, and the typical lack of sialylated glycans with BEVS-expressed N-linked glycoproteins, have raised questions concerning the presence and/or concentration of sialyltransferase in insect cells.

Several strategies have been used to extend the processing of glycans in insect cells to achieve glycans containing additional GlcNAc, Gal and sialic acid residues. One approach has been to co-infect cells with a recombinant baculovirus expressing a glycosyltransferase and one expressing an N-linked glycoprotein. For instance, Wagner et al. (1996b) co-infected Sf-9 cells with a baculovirus expressing a human GlcNAc T-I and one expressing fowl plaque virus hemagglutinin. The co-expression of the GlcNAc T-1 resulted in a four-fold increase in glycans with terminal GlcNAc residues attached to the hemagglutinin.

Using a bovine Gal T-I enzyme expressing BEVS, Jarvis and Finn (1996) detected terminal Gal residues on glycans attached to gp64, an AcMNPV structural glycoprotein. In the absence of Gal T-1 expression, lectin-binding assays detected terminal mannose and GlcNac residues, but no Gal residues on the gp64 glycans. Similar results were obtained during wild-type AcMNPV replication in transformed (also referred to as stably transfected) Sf-9 cells expressing an integrated Gal T-1 gene.

Jarvis and co-workers have also used a combination of transformed Sf-9 cells and a baculovirus expressing mammalian genes involved in glycan processing. Jarvis and Finn (1996) constructed a BEVS expressing GlcNAc T-1, and then used this virus to infect cells previously transformed with Gal T-1. The resulting addition of GlcNAc and Gal residues to the gp64 glycans indicated that the substrates UDP-GlcNAc and UDP-Gal might not be limiting in Golgi of Sf-9 cells.

Jarvis, Kawar and Hollister (1998) constructed a BEVS expressing a mammalian α2,6 sialyltransferase gene. They used this virus to infect transformed Sf-9 cells expressing Gal T-1. The resultant glycans attached to the baculovirus gp64 protein contained Gal and terminal sialic acid residues, as determined by lectin-binding analyses. The results suggest that the expression of foreign sialyltransferase can be used to produce recombinant N-linked glycoproteins with terminal sialic acid residues. In addition, the results suggest that Sf-9 cells contain the CMP-sialic acid substrate and that it is transported from the nucleus to the Golgi apparatus. However, the lectin analyses employed are questionable and have not allowed quantitative measurements.

In the absence of genetic engineering, the question remains unanswered as to whether lepidopteran insect cells have the metabolic potential for mammalian-like complex glycosylation with terminal sialic acid residues. Clearly, GlcNAcase and α1,3 mannosidase activities could be used to explain the abundance of paucimannose structures detected in many BEVS studies with glycoproteins. However, it occurred to the inventor that processing of glycans might be significantly influenced by cell type, cell culture media components, culture conditions, and the properties of the baculovirus, as well as the properties of the protein being expressed. In addition, one needs to keep in mind that during BEVS production of recombinant proteins, the cell is undergoing apoptosis. Considerable research in this area is required to reach a basic understanding of the underlying factors that control the glycan processing with individual glycoproteins.

A part of this understanding will come from the study of the rare BEVS expressed recombinant glycoproteins that process glycans beyond paucimannose structures. For instance, with IgG expressed in BTI-TN-5B1-4 cells, approximately 20% of the glycans have one terminal Gal residue and 65% of the glycans have one or more terminal GlcNAc residues The first publication in which sialylation occurred with the BEVS in cell culture was by Davidson et al. (1990). They characterized glycans attached to human plasminogen (HPg) during BEVS expression in Sf-21 cells. Using a combination of lectin-blotting, anion-exchange liquid chromatography and glycosidase digestions, they found that approximately 40% of the glycans attached to HPg contained terminal sialic acid residues. Davidson and Castellino (1991) expressed this same protein in the *Mamestra brassicae* cell line, IZD-MB0503, and found that 53% of the glycans attached to HPg contained terminal sialic acid residues. They also detected HPg sialylated glycans produced in the CM-1 line derived from *Manduca sexta*.

Sridhar et al. (1993) reported that expression using an earlier and weaker viral gene promoter (the MP promoter instead of the polyhedrin promoter) produced the β subunit of human chorionic gonadotropin with some sialylation. However, the level of sialylation was less than observed in mammalian cells. Vandenbroeck et al. (1994), using lectin-blotting analyses, detected terminal sialic acid residues attached to the glycans of BEVS expressed porcine interferon-γ produced in Sf-9 cells. Russo et al. (1998), also using lectin-blotting analyses, reported terminal sialic acid residues on glycans attached to a bovine leukemia virus envelope glycoprotein produced in Sf-21 cells.

Ogonah el al. (1996) reported complex glycosylation of human interferon-γ produced with the BEVS. The complex glycosylation included the synthesis of terminal N-acetylglucosamine and galactose but not sialic acid. Complex processing was obtained in *E. acrea* but not *S. frugiperda* (Sf-9) tissue culture cells.

A problem with lectin-blotting analyses, the analytical tool used for the majority of the glycan analysis described above, is that it does not allow for quantitative determinations. In addition, although appropriate controls were included in all lectin-blotting experiments, glycobiologists advise that false-positive data are not uncommon with lectin-blotting studies. The potentially suspect results obtained from lectin-blotting experiments must be confirmed with results from other techniques to be convincing.

Although there have been very few investigations concerning endogenous processing (without BEVS) of glycoproteins in lepidopteran cells, there is a report by Kato et al. (1994) in which they found evidence of glycans with terminal sialic acid residues. They reported a 130 k glycoprotein from the hemolymph of *B. mori* larvae that was present in "active" and "inactive" haemagglutination forms at different stages of larval development. Using chemical and enzymatic removal of sialic acid residues from this purified lectin and HPLC to quantitate sialic acid contents, they found high levels of sialic acid residues on glycans of the inactive form and no sialic acid residues on the active form. Similarly, sialylated glycans that are cell type-specific and developmentally regulated have also been identified in *Drosophila melanogaster* (Roth, 1992) using lectin-gold histochemistry and gas liquid chromatography-mass spectroscopy.

Based on the above-mentioned studies, it appears that insects have the potential to process N-linked mammalian glycoproteins, with glycan structures similar to those attached during production in mammalian cells. However, no one has provided a reliable expression system that can realize this potential.

Baculovirus Expression Vector System (BEVS) and Microgravity Bioreactors

There has been a great deal of interest in the production of recombinant glycoproteins with the various expression vector systems. The baculovirus expression vector system (BEVS) employs lepidopteran larvae and their derived cell culture (referred to herein simply as insect cells). Because insect cells have been shown to recognize the signal sequences and possess the metabolic pathways for processing glycoproteins in a manner similar to mammalian cells, there has been a great deal of interest in using the BEVS to produce recombinant N-linked glycoproteins.

Insect tissue culture cells have difficulty growing in "traditional" bioreactors. The major limitation to the scale up of insect cells has been providing sufficient oxygen without damaging the cells. Insect cells in culture have a 3–10 fold higher oxygen demand than mammalian cell cultures. Upon infection of insect cells with recombinant virus, the demand for oxygen can be increased 50%–100%. For small-scale spinner flask cultures, the surface area-to-volume ratio is large enough that diffusion alone can supply sufficient oxygen. However, as the volume of a bioreactor increases, the surface area-to-volume ratio typically decreases, leading to oxygen limitation. This limitation leads to decreases in cell density and lower yields in production.

In order to overcome the large demand for oxygen, aeration by bubbling air (oxygen or a mixture) through the culture medium has been used. However, this method can significantly damage insect cells due to turbulence. Insect cells are much more shear-sensitive than microbial cells, due to their larger size and lack of a cell wall. Virus-infected insect cells are even more shear-sensitive, since they swell to twice their original size upon virus infection. To overcome this dual problem of providing sufficient oxygen without damaging the cells, protective agents have been added to the medium. However, the problem has only been partially overcome.

As a result of shear forces, the protein production levels observed in stationary cell cultures are not always obtained with suspension cell cultures. Until recently, the technology has not been available to evaluate these interactions. However, the development of the microgravity bioreactor, High Aspect Ratio Vessel (HARV), has made it possible to directly evaluate the effects of microgravity upon cellular function and structure.

Microgravity and Shear Forces

In vitro investigations have shown that environmental factors can influence oligosaccharide processing. Goochee and Monica (1990) have reviewed cell culture studies in which environmental factors affected N-linked glycosylation. They discussed several alterations to glycosylation that were chemically induced, i.e. glucose starvation, hormones, and acidotropic amines. Further confirmation of the importance of slight changes in culture conditions came with the discovery of changes in glycoforms during batch culture and from batch to batch (Hooker el al., 1995).

Microgravity effects on glycosylation have not been studied previously. However, there have been several microgravity investigations in other contexts. For instance, Hymer et al. (1996) suggested that disparate post-translational modifications occurred in the rat PRL hormone following space flight. Bechler et al. (1992) and Fuchs and Medvedev (1993) observed increases in the production and secretion of interferon (a pharmaceutically important glycoprotein) by lymphocytes during space flight.

Microgravity can have an effect on structural organization of the endoplasmic reticulum and Golgi apparatus. For instance, Moore et al. (1987) found that corn cell endoplasmic reticulum development under microgravity was abnormal, with structures clumping into spherical and ellipsoidal masses. Similar endoplasmic reticulum disruptions were observed by Hilaire et al. (1995) with sweet clover cells cultured in a rotating clinostat. Under simulated microgravity, rice cell walls grew irregularly, and microgravity-mediated structural changes in chloroplast grana and mitochondria cristae have been noted. Similarly, experiments with *Chlamydomonas reinhardtii* illustrated microgravity-mediated changes in shape, structure and distribution of cell organelles.

It is known that hydrodynamic shear forces, which result when culturing conditions are scaled up in large bioreactors, influence the cytoskeletal structure of cultured cells. In 1988, Schürch et al. determined that shear forces generated in cell culture affect both cell shape and membrane integrity. Hydrodynamic shear induction of gene transcription and enzyme activity is well established. In addition, shear forces have been found to affect both the level of protein synthesis and the extent of glycosylation. The precise mechanism(s) responsible for these changes are unknown.

Since the development of the BEVS in the early '80s, the BEVS has been shown to have a high potential for the commercial production of recombinant proteins. Hundreds of recombinant proteins have been expressed with the BEVS because of the high production levels, ease of purification and the recognition of higher eukaryotic co- and post-translational signal sequences by insect cells. Although insect cells possess N-linked glycosylation processing machinery, under most conditions complex glycosylation has not been obtained with the BEVS. A technology leading to increased efficiency of complex oligosaccharide processing of glycoproteins is needed to further the development of this viral expression system.

Recently, experiments were performed in which insect cells (Sf9) were cultured and infected with a recombinant virus expressing β-galactosidase in the HARV bioreactor, which is designed to simulate a microgravity environment. In this environment, Sf9 insect cells produced approximately 7-fold more β-galactosidase protein than Sf9 cells cultured in shaker flasks. In addition, the Sf9 cells underwent substantial morphological and physiological changes, exhibiting a sustained stationary phase.

We report herein that microgravity can also significantly alter the eukaryotic, N-linked glycosylation pathway in the Golgi complex. Under conditions of microgravity, insect tissue culture cells are induced to produce complex, sialylated glycans on a secreted human glycoprotein. Further, even under normal gravity conditions, insect tissue culture cells are induced to produce complex, sialylated glycans on a secreted human glycoprotein, when the culture media were supplemented with dexamethasone or N-acetylmannosamine.

SUMMARY OF THE INVENTION

This invention discloses the use of a microgravity environment or dexamethasone or N-acetylmannosamine supplemented insect cell culture media to optimize the processing of the oligosaccharide moieties attached to glycoproteins. Glycosylated proteins represent the major class of circulating proteins in higher animals and control many important biological functions. There is a great deal of interest in the commercial production of glycoproteins with pharmaceutical properties. Among the most attractive technologies to produce these glycoproteins is the baculovirus expression vector system (BEVS) with insect tissue culture cells. The BEVS allows for the production of high quantities of protein, and insect cells recognize the higher eukaryotic signals for co- and post-translational modifications, such as glycosylation.

Current data illustrate that most BEVS production systems do not achieve the full cellular potential for processing complex glycoproteins with terminal sialic acid residues. Culturing under microgravity conditions, an embodiment of the current disclosure, significantly alters the processing of oligosaccharides during the synthesis of glycoproteins. In another embodiment of the invention, culturing the cells in insect cell culture media supplemented with dexamethasone or N-acetylmannosamine also significantly alters the processing of oligosaccharides during the synthesis of glycoproteins.

Microgravity conditions can significantly alter a range of synthetic and processing events, as well as cause significant structural alterations to cellular organelles of the secretory pathway where glycoprotein processing occurs. For instance, glycosylation takes place in the Golgi apparatus and endoplasmic reticulum, both of which have been shown to undergo significant structural alterations under conditions of microgravity. In addition, shear can effect both the level of protein synthesis and extent of glycosylation.

Therefore, an embodiment of this invention is the BEVS directed synthesis and glycosylation of a model protein, secreted human placental alkaline phosphatase (SEAP) in a microgravity environment. Baculovirus-infected insect tissue cultures are cultured under microgravity (HARV) culture conditions. Under these conditions, the present invention enables the BEVS expression of proteins that have terminal sialic acid glycosylation.

Another embodiment of the invention is the BEVS directed synthesis and glycosylation of a model protein, secreted human placental alkaline phosphatase (SEAP) in dexamethasone or N-acetylmannosamine supplemented insect cell culture media. Under these conditions, the present invention enables the BEVS expression of proteins that have terminal sialic acid glycosylation.

The disclosed invention increases the fundamental understanding of the effects of a microgravity environment on the biochemical and cellular factors and processes involved with eukaryotic protein synthesis, secretion and co- and post-translational processing. This invention is of value to industrial applications for the production of pharmaceutical glycoproteins. It may also provide a model for the effects of microgravity at the organismal level.

DESCRIPTION OF THE PREFERRED EMBODIMENT

Figure 1A:
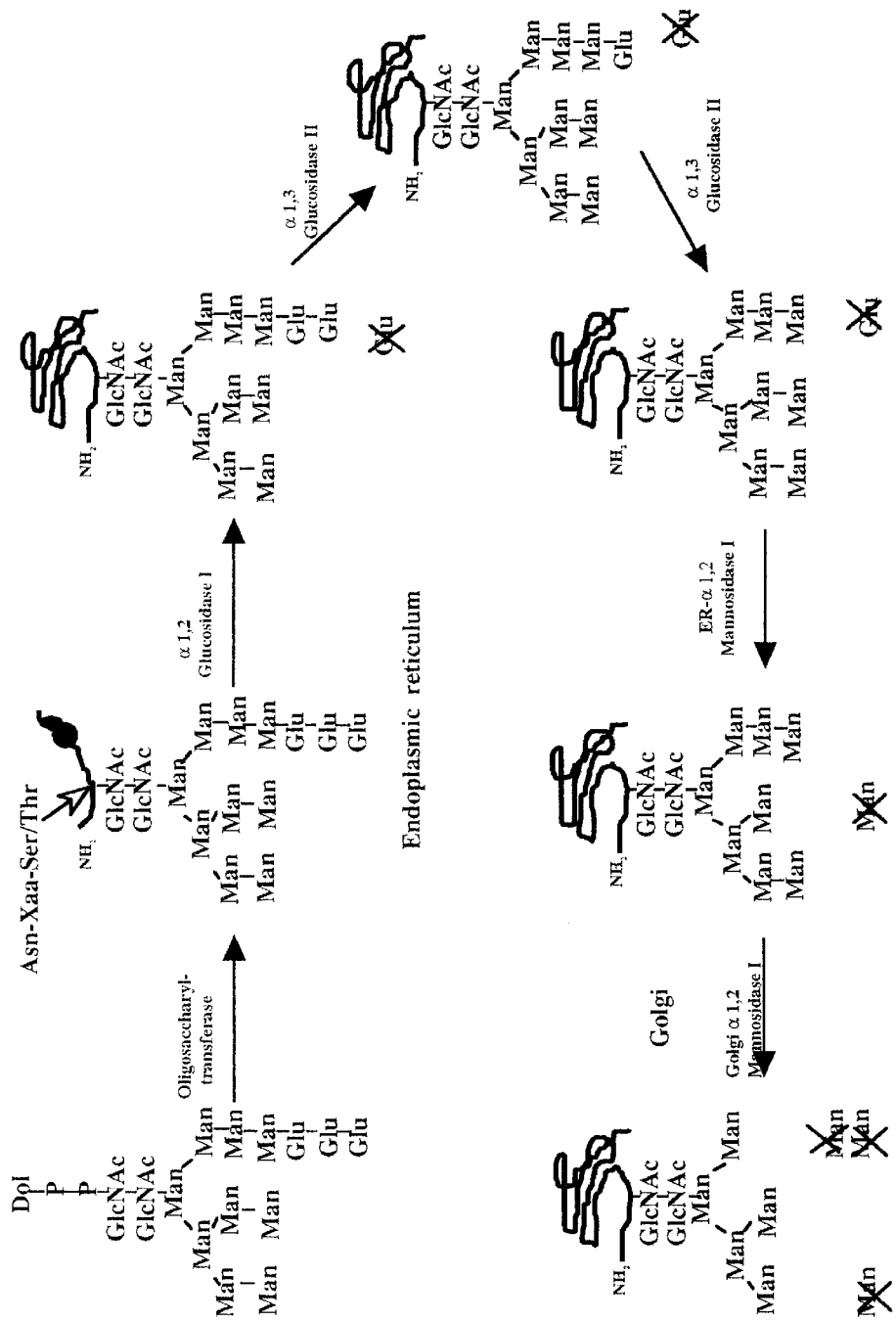
FIGS. 1A and B show the N-linked glycosylation pathway in the endoplasmic reticulum and Golgi apparatus. While the N-linked glycoprotein is being synthesized in the endoplasmic reticulum, a preformed oligosaccharide structure is attached to the amino group of asparagine. The glucose (Glu) and terminal mannose (Man) units are removed in the endoplasmic reticulum and Golgi apparatus. The addition of N-acetylglucosamine (GlcNAc), fucose (Fuc), galactose (Gal) and finally sialic acid (Sial) residues occurs in the Golgi apparatus.
Figure 1B:
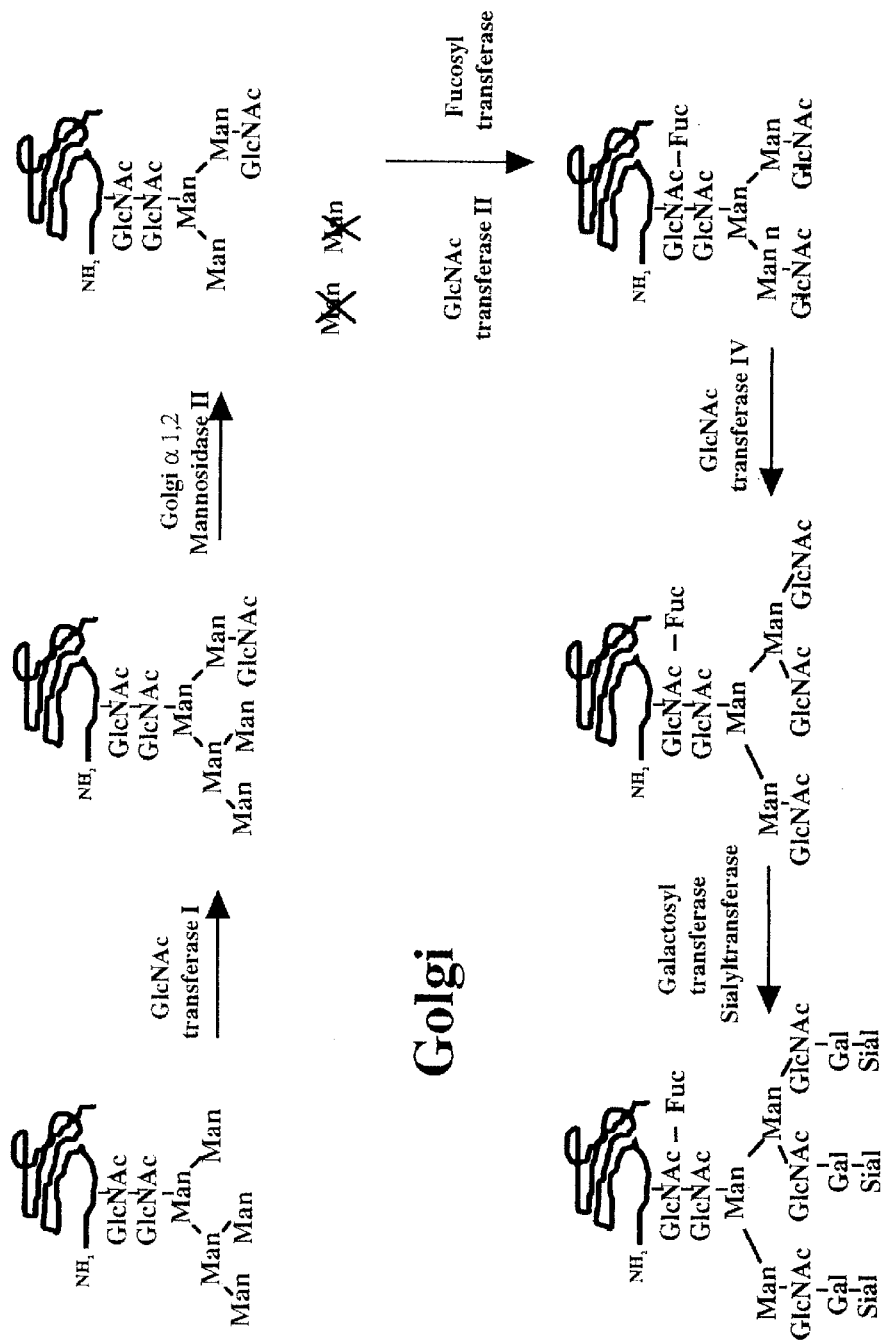

The present invention discloses the effects of microgravity on the glycosylation of proteins, one of the most important co- and post-translational events. Insect tissue culture cells possess the intrinsic biochemical pathways necessary for synthesis of sialylated, complex glycoproteins. However, these pathways are not fully functional during expression of heterologous proteins without using the culture techniques of the present invention.

In comparison to microbial cells, insect cells are much more shear-sensitive due to their larger size and lack of a cell wall. Virus-infected insect cells are even more shear-sensitive, since they swell to twice their original size upon virus infection. Therefore, this invention tackles these problems by developing a novel model system. By utilizing a microgravity environment for the baculovirus expression systems, this invention allows for the production of more complex glycoproteins with sialic acid residues. The increased complexity more accurately mirrors true co- and post-translational modifications of human genes, thereby enabling their use in pharmaceutical preparations.

An embodiment of this invention uses insect tissue culture systems and a model BEVS designed to study co- and post-translational processing events. This invention is designed to provide an improved system of producing pharmaceutically and industrially relevant recombinant proteins. These proteins may include, but are not limited to, erythropoietin, human thyrotropin, tissue plasminogen, blood clotting factors, interleukins, and interferons. As an example, the production, secretion and glycosylation of human placental alkaline phosphatase (SEAP) is evaluated under microgravity (HARV) and stationary culture conditions. The oligosaccharides associated with this protein produced in insect cells are compared with the same protein purified from mammalian cells.

Previous studies on SEAP production and co- and post-translational modifications have only been conducted in stationary insect cell cultures and insect larvae. The initial experiments disclosed herein optimize the conditions for a novel method of culturing cells in a microgravity bioreactor, specifically the High Aspect Ratio Vessel (HARV). Cell cultures are adapted to and maintained in this environment in parallel with cultures grown under stationary culture conditions. The conditions necessary for optimal virus infection are determined. The total amount of SEAP produced and secreted is quantitated. The SEAP is purified, and the structure and composition of the oligosaccharide moieties are determined.

Model System

The genetic potential of insect cells to perform N-linked glycosylation while using the BEVS to produce heterologous glycoproteins was evaluated. Previous investigations had shown that vertebrate glycoproteins, which normally are modified with oligosaccharides containing terminal sialic acid (complex structures), typically have high mannose and paucimannose oligosaccharides when produced with the BEVS in insect tissue culture cells. This observation raised the question as to the metabolic potential for complex glycosylation of glycoproteins produced in lepidopteran insect cells. To investigate this, the intrinsic glycosylation potential of insect tissue culture cells and larvae was examined.

Lectin-blotting analyses with normal (uninfected) BTI-Tn-5BI-4, Tn-368 and Sf-21 tissue culture and *T. ni* larval cell homogenates were performed in the presence of a neuraminidase inhibitor. Peanut agglutinin (PNA) binding to several proteins from each insect tissue culture cell sample indicated the presence of the core disaccharide, galactose β(1-3) N-acetylglucosamine of O-glycosidically linked carbohydrates. The lectin *Datura stramonium* agglutinin (DSA), which specifically recognizes galactose (Gal) linked β(1-4) to N-acetylglucosamine (GlcNAc), bound to several proteins of differing molecular weights from the three cell lines. The lectins *Sambucus nigra* agglutinin (SNA) and *Maackia amurensis* agglutinin (MAA) recognize sialic acid linked to Gal α2,6 and α2,3, respectively. SNA and MAA lectins bound to several proteins from all tissue culture cell lines. While most scientists skilled in the art believed that BEVS could not be used for the production of recombinant, sialylated glycoproteins, the present inventor believed that insect larval and tissue culture systems had the intrinsic potential for formation of N- and O-linked oligosaccharides.

To test this hypothesis, a simple model system has been developed. The model system is based on a recombinant isolate of the *Autographa californica* nuclear polyhedrosis virus, which can infect most tissue culture cells established from lepidopteran insects. The recombinant virus expresses a secreted-form of human placental alkaline phosphatase (SEAP) gene during virus replication. The mature SEAP protein has 513 amino acids, with a molecular weight of 55,510 Daltons. The human placental alkaline phosphatase has a transport signal peptide and a highly hydrophobic membrane anchoring region at the carboxy terminus of the protein. The anchoring region can be removed, resulting in secretion from the cells. There are two putative N-linked glycosylation signals within the mature protein, but only one site is glycosylated. The SEAP system provides an easily assayable gene product which can be used to evaluate the production level, secretion level and glycosylation during synthesis in several different insect cells under varying culture conditions.

Using the SEAP model system, it was determined that host cell determinants play a critical role in the level of recombinant protein production. The BTI-Tn-5B1-4 cell line High Five™) (Invitrogen, San Diego, Calif.) has been identified as a novel insect cell line. The BTI-Tn-5BI-4 cell line was isolated from *Trichoplusia ni* and was unique in that it expressed higher levels of foreign proteins than any of the other insect cell lines tested.

The reason for this increased production is unknown. However, it has been hypothesized that any metabolic output to repair cellular damage results in a loss of those resources for cellular differentiation and replication. The BTI-Tn-5B1-4 cells may require lower repair processes than other cell types. This would be consistent with the increase in β-gal levels produced by insect cells subjected to a microgravity environment. Insect cells cultured in this environment may not expend as much of their metabolic resources on repairing cellular damage caused by shear, resulting in higher levels of transcription and translation. Also, under conditions of microgravity, cell viability is maintained much longer. Therefore, the absence of shear and cell lysis may be important for late protein production.

SEAP produced in vertebrate cells has complex glycan structures containing terminal sialic acid residues. However, when produced in insect tissue culture cells, lectin-blotting assays indicate the presence of only terminal mannose residues. Consequently, lectin-blotting tests were conducted with SEAP produced in *T. ni* larvae by immunoprecipitating SEAP from insect hemolymph. There was no positive reaction with the lectin MAA, but SNA lectin bound to a protein with an apparent molecular weight of 64 kDa (the molecular weight of the mature form of SEAP). This observation suggested that larval produced SEAP contained terminal sialic acid linked α2,6 but not α2,3 to Gal. Therefore it was considered that recombinant SEAP produced in insect larvae but not insect cell cultures could be modified with oligosaccharides having terminal sialic acid residues.

A problem with lectin-blotting analyses is that they do not allow for quantitative determinations. In addition, although appropriate controls were included in all lectin-blotting experiments, glycobiologists advise that false-positive data are not uncommon with lectin-blotting studies. In fact, subsequent experimentation showed that, although SNA bound to gp64 (a baculovirus structural protein) produced in cell culture and SEAP produced in larvae, two more sensitive techniques did not detect any terminal sialic acid residues.

Since quantitative data are important in glycan analyses, there is a need to use a more definitive and informative approach. To initially fulfill this need, a new glycan analysis technology, fluorescence assisted carbohydrate electrophoresis (FACE) was chosen.

For FACE analysis, the SEAP had to be purified under conditions which had no bias for a particular glycoform. Accordingly, an affinity chromatography procedure which gave high yields of SEAP free of any detectable glycoprotein contaminants was developed. The glycans were removed from purified protein by hydrazinolysis or digestion with *Flavobacterium maningoseptum* peptide-N-glycosidase F (PNGase F). A fluorescent dye with a negative charge was then attached to the reducing end of the oligosaccharides. The glycans were fractionated by polyacrylamide gel electrophoresis, and the gels scanned with a fluorescent imager. The glycans were fractionated based on their size and conformation.

The initial FACE analysis compared the SEAP oligosaccharides attached during production in two *Trichoplusia ni* (TN-368 and BTI-Tn-5b1-4) and one *Spodoptera frugiperda* (IPLB-SF-21A) tissue culture cell line (Kulakosky et al., 1998a). Ten glycan structures were attached to the single SEAP glycosylation site. The detected SEAP oligosaccharides contained only mannose and fucose attached to the core GlcNAc residues. The majority of glycan structures produced by the three cell lines contained two or three mannose residues, with and without core fucosylation (fucose residue on N-acetylglucosamine residue bonded to asparagine), but there were structures containing up to seven mannose residues. The glycan structures were determined based on electrophoretic mobility compared with standards and sensitivity to exoglycosidases.

A comparison was then made of the N-linked glycans attached to SEAP produced in four species of insect larvae and their derived cell lines plus one additional insect cell line and larvae (Kulakosky et al., 1998b). These data surveyed N-linked oligosaccharides produced in four families and six genera of the order Lepidoptera. The purpose was to compare glycosylation of SEAP during synthesis in distantly related lepidopteran insects and undifferentiated versus differentiated cells. Recombinant SEAP expressed by recombinant isolates of AcMNPV and *Bombyx mori* NPV was purified from cell culture medium, larval hemolymph or larval homogenates. Recombinant SEAP produced in cell lines of *Lymantria dispar* (IPLB-LdEIta), *Heliothis virescens* (IPLB-HvT1), and *B. mori* (BmN) and larvae of *S. frugiperda, T. ni, H. virescens, B. mori,* and *Danaus plexippus* contained oligosaccharides with only mannose-terminated oligosaccharides. The glycans in each sample were qualitatively very similar. Most larval and tissue culture samples contained a large percentage of the oligosaccharides with two or three mannose residues without terminal α1,3linkages. Only SEAP produced in Sf-21 cells lacked these small structures without terminal α1,3 linkages. Therefore it was hypothesized that, during their long period in culture, the Sf cells may have mutated, reducing or eliminating the expression of an α1,3 mannosidase.

Although qualitatively identical, the SEAP produced in larvae generally had smaller amounts of oligosaccharide with five to seven mannose residues than samples produced in tissue culture cells. Of particular note is that, unlike the lectin-blotting studies, the more reliable FACE data presented no evidence for terminal sialic acid, Gal or GlcNAc residues on the SEAP glycans.

HPLC is an alternative to FACE analysis, and is the preferred mode of analysis of the N-linked glycosylation of SEAP in the current invention. HPLC results are clear, and there is no background to contend with when analyzing the results. SEAP is purified from the cell culture medium, and the oligosaccharides enzymatically released. Fluorescent-labeled oligosaccharides are fractionated and the structures determined using normal phase HPLC techniques. Although microgram amounts of glycoprotein can be harvested, the purification and fluorescence-labeling HPLC techniques require only picomole amounts of glycans.

The SEAP model system is an ideal example of using this novel technology. First, SEAP protein can be produced and purified in sufficient amounts following synthesis in many different cell types cultured under various conditions. Since SEAP has a single glycosylation site, minor modification can be detected. Using HPLC, it is possible to monitor subtle changes in oligosaccharide processing, both qualitatively and quantitatively, under conditions induced by microgravity.

Cells

Two insect cell lines, S. frugiperda (Sf21) and Trichoplusia ni (BTI-Tn-5B1-4), are used in these studies. Additional cell types can be used if appropriate. Although the Sf9 cell line (derived from the Sf21 cell line) has been used extensively to express recombinant proteins, it is not discussed in the present disclosure because, although they are easy to culture, they are amongst the poorest production systems with the BEVS. Based on these and other studies, the BTI-Tn-5B1-4 cell line has replaced the Sf9 cells as the "gold standard". However, the Sf9 cells and other insect cells could still work in this invention (see Kulakosky el al., 1998b). The Sf21 cells are included because they have been shown to exhibit different oligosaccharide processing with SEAP. The Sf21 are readily adaptable to growth under microgravity conditions.

The cells are cultured in Ex-Cell 405 serum-free medium (JRH Biosciences, Lenexa, Kans.) and TNMFH serum-containing medium (Life Technologies, Grand Island, N.Y.) insect tissue culture medium. Growth in both media results in high levels of SEAP synthesis with the BEVS. SEAP purified from human placenta is used in parallel as the representative mammalian protein.

Virus

The construction of the recombinant Autographa californica nuclear polyhedrosis virus (AcMNPV) expressing SEAP (AcSEAP), a technique being known in the art, is hereby incorporated by reference (Davis et al., 1992). Briefly, the SEAP gene is inserted into the AcMNPV genome such that the polyhedrin gene is removed and the open-reading-frame of the SEAP gene is placed under the transcriptional control of the polyhedrin gene promoter.

Reactor Conditions

Initial studies concentrate on adapting the Sf21 and BTI-Tn-5B1-4 cell lines to growth in the High Aspect Ratio Vessels (HARV) of the Rotary Cell Culture System (Synthecon Inc., Houston, Tex.). The HARV system has been used previously to culture Sf9 insect tissue culture cells.

Insect cell cultures can be grown to high cell density and their oxygen uptake requirements normally exceed mammalian cells and increase upon baculovirus infection. Since air does not contain sufficient oxygen, oxygen-enriched gas is supplied to the HARV reactor. Oxygen-enriched atmospheres have been used routinely with high-density cultures of insect cells in spinner flasks. The effects of rotation speed, medium supplements, and oxygen enrichment on SEAP production and glycan structure are examined.

Since virus attachment to the cell surface approaches diffusion-limited values, a microgravity reactor might be expected to give poor infection and protein production kinetics. This outcome is unlikely, since the work of O'Connor showed that cells in simulated microgravity oscillate on the order of a millimeter in a HARV providing convective mixing. Nonetheless, the role of infection kinetics is studied by: (1) suspending pre-infected cells in the HARV, (2) infecting a culture in a HARV at multiplicities of infection (MOI) from 1 to 10 (NASA Tech Brief MSC-22336), and (3) infecting at different MOI (1 to 10) an identical culture in a spinner flask. Comparison of these results allows for an assessment of whether virus-cell contact is efficient.

Based on the preliminary studies of oxygen supply and viral infection, a standard, near optimal protocol for use of a HARV with these cultures is specified. HARV culture vessels are filled with a suspension of infected cells at a density of one million cells per milliliter. The vessel is rotated at approximately 12 revolutions per minute to achieve simulated microgravity. The gas supply to the HARV chamber membrane is 90 percent oxygen and 10 percent nitrogen. To reduce evaporation through the membrane, the gas is bubbled through a water column.

SEAP Production and Secretion

Samples of medium are withdrawn from the bioreactor at various times post-infection (typically 0–36 hours). These samples are assayed to determine the amount of SEAP production. To evaluate both the production and secretion of SEAP, one-half of the samples are spun in a centrifuge to remove the cells, and the supernatant is assayed for SEAP activity. The other half (containing both cells and medium) is sonicated to lyse the cells. This sample reflects the total amount (cell-associated plus secreted) of SEAP produced. The amount of secreted SEAP can then be calculated by subtracting medium-associated SEAP from total SEAP. This provides data concerning the time post-infection when the peak levels of SEAP have been synthesized. This is the time when SEAP should be harvested for purification and oligosaccharide analysis. These experiments show that greater than 90% of the SEAP produced is secreted. The sensitivity of the SEAP assay allows for quantitative results at picogram per milliliter levels.

In previous studies conducted under stationary culture conditions, SEAP protein synthesis was first detected at 18 hours post-infection with BTI-Tn-5B1-4 cells. Following synchronous infection of the cells, the maximum level of SEAP activity occurred at approximately 120 hours post-infection under stationary flask, spinner flask and HARV reactor conditions.

Glycan Analysis

Current knowledge concerning the production of glycoproteins with baculoviruses teaches that the glycosylation pathway in lepidopteran larvae and tissue culture cells results in the production of glycans usually containing terminal mannose residues, occasionally containing terminal N-acetylglucosamine or galactose residues and very rarely containing terminal sialic acid residues. Most of the reports claiming terminal sialic acid residues were documented using lectin binding assays which are considered highly suspect by those well versed in the science of glycobiology.

The analysis of the glycosylation of SEAP produced in a wide variety of lepidopteran larvae and tissue culture cells is typical of the glycan processing of most glycoproteins with the baculovirus expression system. Only terminal mannose residues are detected.

SEAP Purification

The influence of microgravity on the oligosaccharide processing of SEAP is evaluated by HPLC. Previously developed purification procedures for alkaline phosphatase are inappropriate for these studies. These protocols used chromatographic procedures making separations based on charge and size. The procedures employed serial purification steps during which most of the alkaline phosphatase was discarded while obtaining high purity samples. Unfortunately, these procedures can also enrich for a subset of the glycoform and are therefore unacceptable for these studies.

A new affinity chromatography procedure that utilizes the alkaline phosphatase active site has been developed (Kulakosky et al., 1998a). The affinity support is aminobenzyl-phosphoric acid coupled to epoxy agarose via histidine. The histidine is first coupled to the activated epoxy agarose via standard chemistry. The histidine agarose is then coupled to the amino group of the aminobenzyl-phosphoric acid with a diazotization reaction.

The tissue culture medium containing SEAP is first dialyzed against a dilute Tris buffer containing magnesium and passed over the affinity column, which binds the alkaline phosphatase nearly quantitatively. After the column is washed with Tris/magnesium buffer, the SEAP is eluted with a phosphate gradient in the same buffer. The recipe for the Tris/magnesium buffer is 20 mM Tris, 1 mM $MgCl_2$, pH 8.0.

The column-purified samples are analyzed by SDS-PAGE using Western blotting, silver stain and carbohydrate detection. The Western blots indicate a single protein moiety, which migrates at the same position as the antibody-purified SEAP samples. In addition, this protein band is glycosylated as determined by previously used lectin binding analyses.

Using silver staining of SDS-PAGE gels, two minor protein contaminants are visible. However, using a digoxigenin glycan detection analysis, the only glycoprotein is the SEAP protein. Using this SEAP purification protocol, the subsequent oligosaccharide analyses are consistent from preparation to preparation with several cell lines. In addition, the data indicate that the SEAP preparations are both quantitative and qualitatively appropriate for the study of carbohydrate composition. Approximately 2–5% of the product is lost during the purification schedule. Therefore, there is no selective elimination of significant amounts of a particular SEAP glycoform.

HPLC

Once the SEAP protein is purified, the oligosaccharide moieties are cleaved from the glycoprotein with peptide N-glycosidase F (cleaves oligomannose, hybrid and complex oligosaccharides with or without terminal sialic acid residues). The oligosaccharides are then bonded to a fluorophore marker. The labeled sugar can be digested with various glycosidases that cleave specific linkages. The samples are analyzed by HPLC. Normal phase HPLC fractionations are carried out with a 50 mM ammonium phosphate, pH 4.4, and acetonitrile gradient on a Glyco Sep-N column (OGS, Oxford, UK) by a technique being known in the art, and incorporated by reference (Guile et al., 1996; Mattu et al., 1998). The Glyco Sep-N column is capable of resolving both neutral and charged sugar residues based on hydrophilicity (related to the hydrodynamic volume and molecular size). To obtain accurate glucose equivalency values, the GlycoSep-N is calibrated with a 2-aminobenzamide (2-AB) labeled dextran hydrolysate ladder and glucose homopolymers. The 2-AB fluorescence is detected and quantified using a Waters[a] 474 Scanning Fluorescence Detector (Waters Corporation, MA) at $\lambda_{ex}$ 330 nm and $\lambda_{em}$ 420 nm using a 16 µl flow cell.

Accordingly, SEAP protein is purified from Sf21 and BTI-Tn-5B1-4 infected insect cells grown under stationary and microgravity conditions. The secreted form of SEAP comprises the samples for analysis. Alterations in glycosylation, which occur under these culture conditions, are documented. The oligosaccharide moieties associated with the SEAP produced in the human placenta are compared with the glycans processed in the insect cells. The results indicate that microgravity has a dramatic effect on glycosylation in SEAP under certain conditions.

Figure 2:
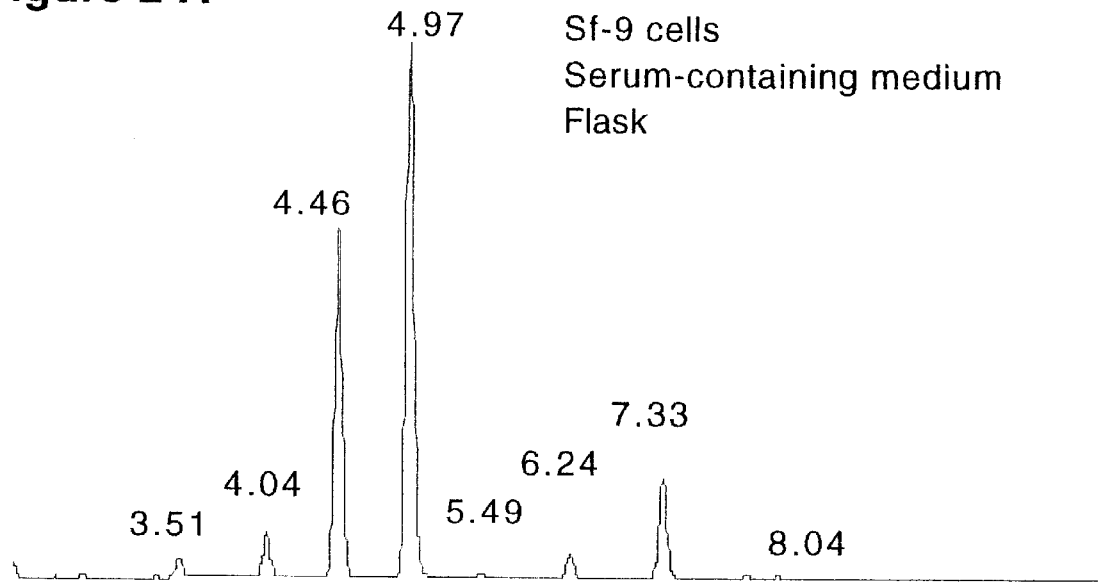
FIGS. 2A and 2B show HPLC fractionation data of SEAP oligosaccharides produced with SEAP expressing recombinants of the baculovirus *Autographa californica* nucleopolyhedrovirus (AcMNPV) in Sf-9 (A) and BTI-Tn-5B1-4h (B) tissue culture cells. The numbers are glucose unit (GU) values described in Table 1.
Figure 2:
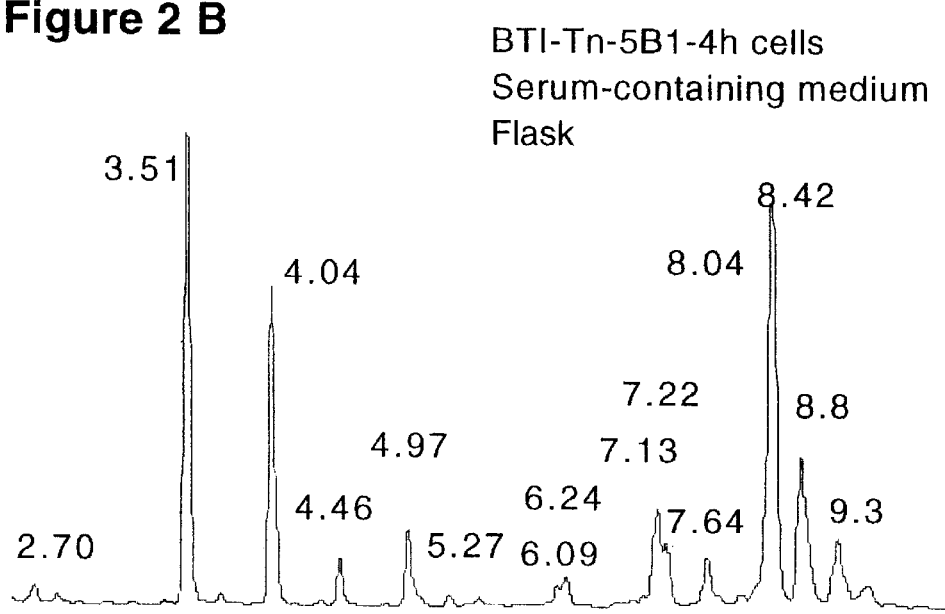

When SEAP oligosaccharides are analyzed by HPLC under conditions containing serum in stationary cultures, there is variability in the N-linked terminal residues depending upon cell type (Table 1, FIGS. 2A and B). A new cell line referred to as BTI-Tn-5B1-4H (also referred to as Tn-4H, or simply 4h) was derived from the BTI-Tn-5B1-4 cell line. 4h cells infected with AcMNPV yield SEAP containing glycan structures with terminal galactose and/or N-acetylglucosamine residues (Table 1). Approximately 51% of the SEAP oligosaccharides produced in BTI-Tn5B1-4H cells contain these structures (Table 1, see structures NM3N2F, NM5N2F, G2N2M3N2, G2N3M3N2, G3N3M3N2, G3N3M3N2F, and G3N4M3N2F). No terminal sialic acid residues are detected. In contrast, Sf9 cells infected with AcMNPV under the same conditions yielded negligible (0.6%) amounts of SEAP containing glycan structures with terminal galactose and/or N-acetylglucosamine residues (Table 1, see structures NM3N2F, NM5N2F, G2N2M3N2, G2N3M3N2, G3N3M3N2, G3N3M3N2F, and G3N4M3N2F). The peaks corresponding to the glucose units shown in Table 1 are also shown in FIGS. 2A and B.

A sample of the new cell line, designated BTI-Tn-5B1-4h, was deposited on Aug. 8, 2000 with the American Type Culture Collection, at 10801 University Blvd., Manassas, Va. 20110-2209, under accession No. PTA-2355.

TABLE 1

SEAP OLIGOSACCHARIDES PRODUCED IN BTI-TN-5B1-4H (4H) AND SF-9 CELLS

| Glucose Units | Proposed Structure | Percentage Cell type | |
|---|---|---|---|
| | | 4H | Sf9 |
| 2.70 | M1N2 | 0.58 | ND |
| 3.51 | M2N2 | 21.87 | 1.70 |
| 4.04 | M2N2F | 15.41 | 3.06 |
| 4.46 | M3N2 | 2.1 | 32.8 |
| 4.97 | M3N2F | 3.42 | 45.25 |
| 5.27 | M4N2 | 0.60 | ND |
| 5.49 | NM3N2F | ND | 0.63 |
| 6.09 | M5N2 | 0.74 | ND |
| 6.24 | M5N2 | 1.45 | 1.98 |
| 7.13 | M6N2 | 2.58 | 13.08 |
| | NM5N2F | 2.58 | ND |
| 7.22 | G2N2N2 | 2.94 | ND |
| 7.64 | G2N3M3N2 | 2.22 | ND |
| 8.04 | M7N2 | 0.40 | 0.70 |
| 8.42 | G3N3M3N2 | 27.95 | ND |
| 8.80 | G3N3M3N2F | 10.56 | ND |
| 9.30 | G3N4M3N2F | 4.53 | ND |

G = galactose
N = N-acetylglucosamine
M = mannose
F = fucose
ND = not detected

Figure 3:
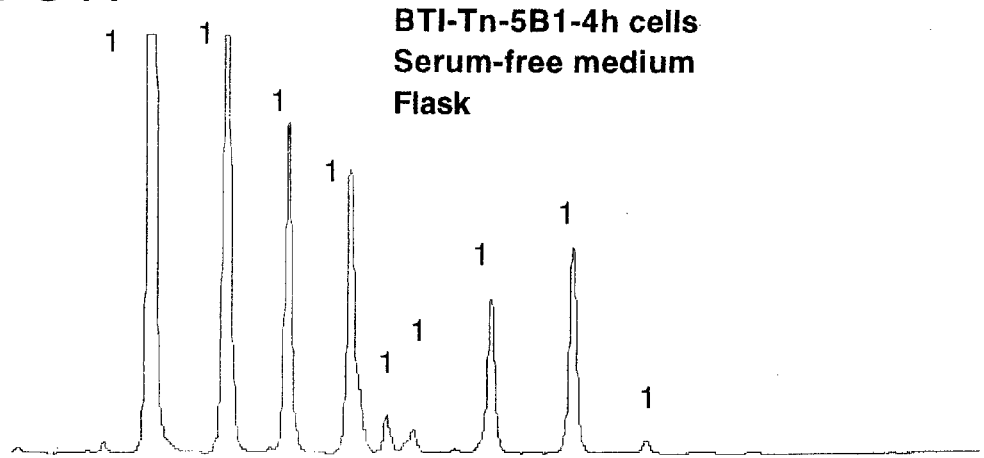
FIGS. 3A, 3B, and 3C show HPLC fractionation data of SEAP oligosaccharides produced in (A) BTI-Tn-5B1-4h cells (4H) cultured in serum-free media in flasks, in (B) BTI-Tn-5B1-4h cells (4H) cultured in serum-containing media in flasks, and in (C) BTI-Tn-5B1-4h cells (4H) cultured in serum-containing media in the microgravity HARV bioreactors.
Figure 3:
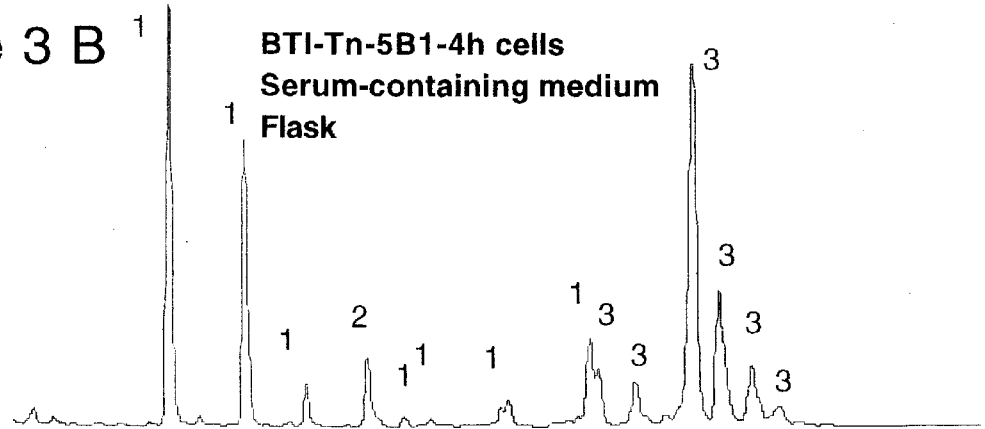
Figure 3:
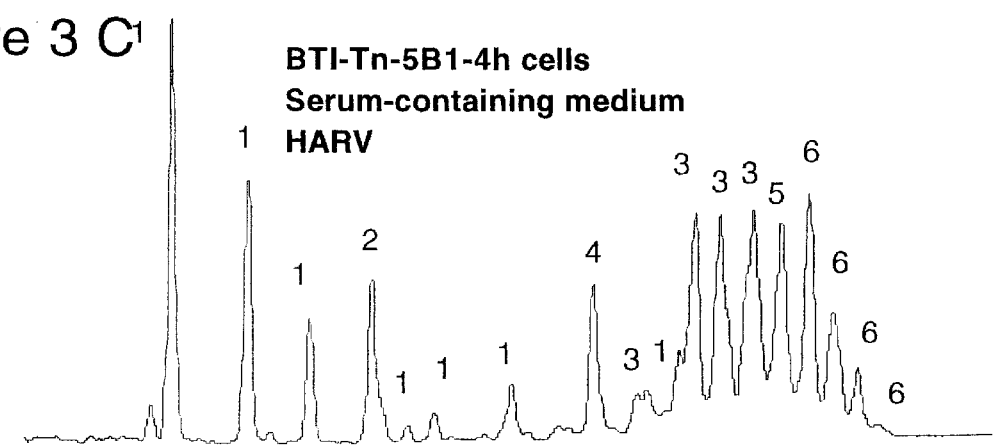

When the 4h cell line is grown in serum-free media under stationary culture conditions, the baculovirus expressed SEAP contains only terminal mannose residues (FIG. 3A). When the 4h cells are grown under stationary culture conditions in serum-containing media, then approximately 45% of the SEAP glycans contain terminal N-acetylglucosamine or galactose residues (FIG. 3B). The remaining glycans only contain terminal mannose residues; terminal sialic acid residues are not detected (FIG. 3B). However, when the infected 4h cells are culture in a HARV bioreactor (microgravity reactor), approximately 20% of the oligosaccharides contained terminal sialic acid residues (FIG. 3C); 37% contained only terminal mannose residues; and approximately 43% had terminal N-acetylglucosamine and/or galactose residues. This result has never been seen previously with any cells grown under any other condition. When an analysis of SEAP purified from human placenta was performed, approximately 17% of the oligosaccharides contained terminal sialic acid residues, and the remaining terminated with mannose, N-acetylglucosamine, and/or galactose residues.

The peaks in FIGS. 3A–C correspond to the following HPLC fractions. Peaks labeled 1 are oligosaccharide fractions with glycans containing only terminal mannose residues. Peaks labeled 2 are an oligosaccharide fraction with 80% of glycans containing only terminal mannose residues, while the remaining structures have terminal galactose and/or N-acetylglucosamine residues. Peaks labeled 3 are oligosaccharide fractions with glycans containing terminal galactose and/or N-acetylglucosamine residues. The peak labeled 4 is an oligosaccharide fraction with 30% of glycans containing only terminal mannose residues, while the remaining structures have terminal galactose and/or N-acetylglucosamine residues. Peaks labeled 5 are oligosaccharide fractions with 66% of glycans containing only terminal galactose and/or N-acetylglucosamine residues, while the remaining glycans have terminal sialic acid residues. Peaks labeled 6 are oligosaccharide fractions where all of the glycans have terminal sialic acid residues.

If the Sf-21 cells are grown in serum-containing medium under microgravity, they produce SEAP glycans that are like SEAP glycans produced by 4h cells in serum-containing medium under stationary culture conditions. Under these conditions approximately 73% of the glycans contained only terminal mannose residues and 27% contained N-acetylglucosamine and/or galactose residues. No terminal sialic acid residues were detected. So, their processing is different from 4h cells under the same conditions. The Sf-21 cells grown in the HARV bioreactor produce an α1,3 mannosidase that is not seen under other culture conditions with Sf-21 or Sf-9 cells and which is expressed by all other insect cell lines and larva under all tested conditions.

Apparently, there is a blood serum component necessary for induction of N-acetylglucosaminyl- and galactosyl-transferase activities in the new 4h cells grown in spinner flasks or in stationary culture. These residues are not observed with Sf-21 or Sf-9 cells under stationary culture conditions. However, if the Sf-21 cells are cultured under microgravity conditions in the presence of serum, the transferase activities are induced.

Under the added condition of microgravity in the presence of the blood serum component, there is an induction of N-acetylglucosaminyl and galactosyl-transferases activities as well as, most importantly, sialyltransferase activity in 4h cells. Microgravity appears to be a cell culture condition that activates transcription and/or translation of proteins, including specifically enzymes such as glycosyltransferases. This invention enables the production of human glycoproteins in insect cells that have the same amino acid and carbohydrate structures as when the proteins are produced in human cells.

Figures 4A, 4B, 4C, 4D:
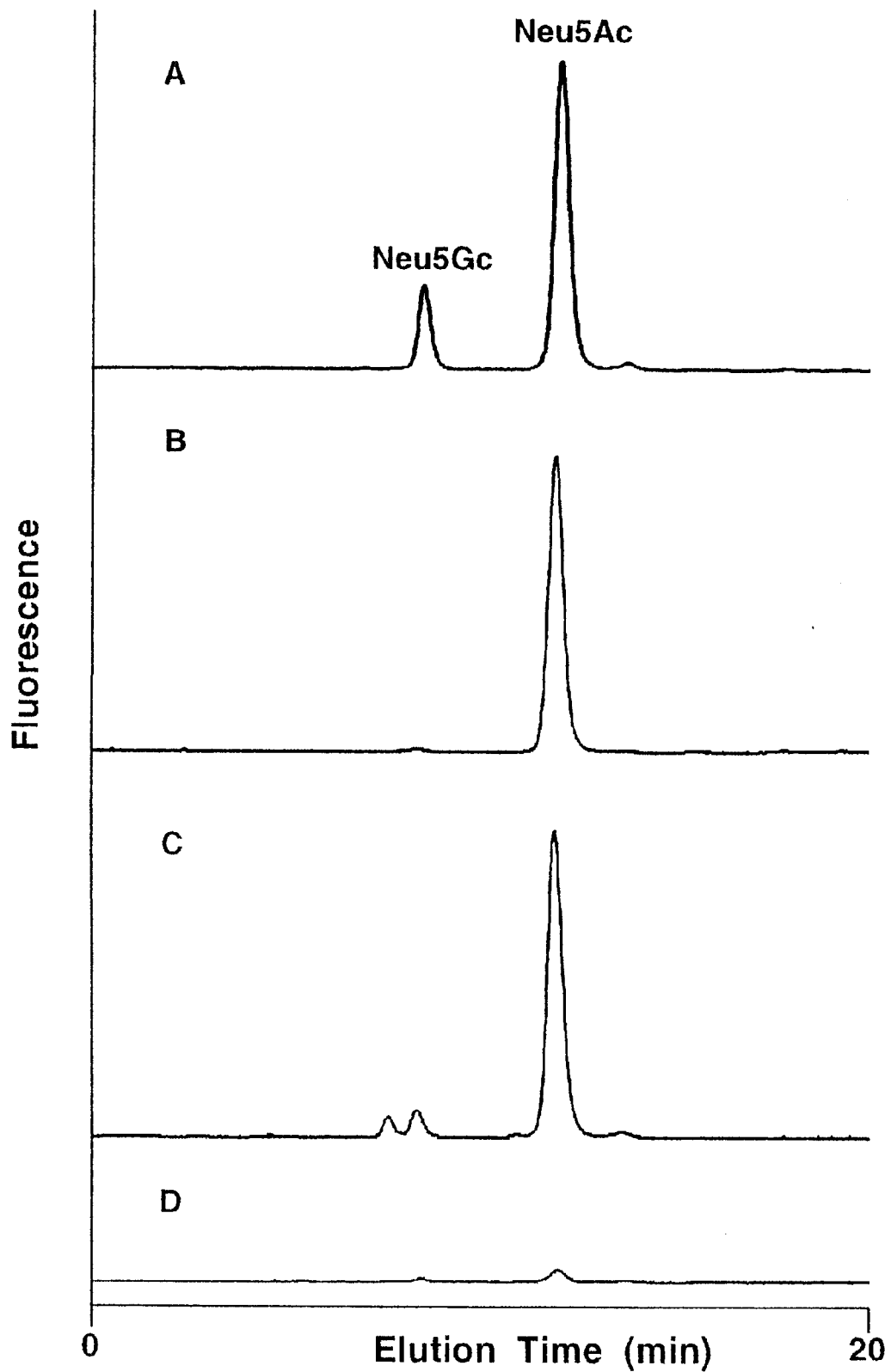
FIGS. 4A, 4B, 4C and 4D show normal phase HPLC profiles of 2-aminobenzamide-labeled N-linked glycans. Glycans were enzymatically released from SEAP produced in Tn-4h tissue culture cells under conditions of microgravity (A) and normal gravity (B). Panel 4C shows SEAP glycans from TN-4h cells cultured under normal gravity with culture medium supplemented with 5 mM N-acetylmannosamine. Panel 4D is the profile of SEAP glycans produced in human placental cells. The peak numbers are the glucose unit values. Green, yellow and red fractions are glycan structures terminating with only mannose, galactose and/or N-acetylglucosamine, and with sialic acid residues, respectively.

The insect cell line Tn-4h was used to produce SEAP (FIG. 4B and Table 2), and the remaining glycans were hybrid and complex asialoglycan structures with terminal N-acetylglucosamine (GlcNAc) and/or galactose (Gal) residues (FIG. 4B and Table 2). None of the glycan fractions were sensitive to digestions with Clostridium perfringens neuraminidase.

TABLE 2

Proposed SEAP Glycan Structures
Based on GU Values and Exoglyeosidase Digestions[1]

| Glucose Units | Proposed Structures* |
|---|---|
| 3.5 | M2N2 |
| 4.0 | M2N2F |
| 4.5 | M3N2 |
| 5.0 | M3N2F |
| 5.0 | NM3N2 |
| 5.3 | M4N2 |
| 5.5 | NM3N2F |
| 6.1 | M5N2 |
| 6.6 | M5N2F |
| 7.1 | NM5N2F |
| 7.2 | G2N2M3N2 |
| 7.6 | G2N3M3N2 |
| 7.7 | G2N2M3N2F |
| 8.0 | M7N2 |
| 8.4 | G3N3M3N2 |
| 8.8 | G3N3M3N2F |
| 9.3 | G3N4M3N2F |
| 9.7 | G4N4M3N2 |
| 9.7 | SG3N3M3N2F |
| 10.1 | SG3N4M3N2F |
| 10.5 | SG4N4M3N2 |
| 10.8 | S2G3N4M3N2F |
| 11.0 | S2G3N4M3N2F |
| 11.4 | S2G4N4M3N2 |

*LEGEND—S, Sialic acid; G, Galactose; N, GlcNAc; M, Mannose, and F, Fucose

When SEAP was produced in Tn-4h cells in HARV bioreactors, five additional glycan fractions were detected (FIG. 4A and Table 2) that were completely and partially digested following incubation with C. perfringens (α2,3 and 2,6 desialylation) and New Castle Disease Virus neuraminidases (α2,3 desialylation) (Corfield et al., 1981), respectively, indicating the presence of terminal α2,3- and 2,6-linked sialic acid residues. The sialylated fractions accounted for 20% of the total glycans attached to the single glycosylation site on SEAP (Millan et al., 1995). These results are comparable to the 18% sialoglycan structures isolated from SEAP produced in the human placenta (Sigma, St Louis, Mo.) (FIG. 4C).

The attachment of terminal sialic acid residues to N-linked glycoproteins produced in cultured insect cells is very unusual (Marz et al., 1995; Luckow, 1995; Davidson et al., 1990; Davidson et al., 1991). Therefore, to verify the sialylation of SEAP glycans based on their elution time and susceptibility to digestion by specific exoglycosidases, the terminal SA residues were analyzed directly. Purified SEAP samples were subjected to mild acid hydrolysis. The released sialic acids were converted to highly fluorescent derivatives with 1,2-diamino-4,5-methylenedioxybenzene (DMB), a fluorogenic reagent for α-keto acids, in dilute acetic acid (Hara et al., 1986; Hara et al., 1987; Reuter et al., 1994). These DMB derivatives were then fractionated by reverse phase HPLC (Hara et al., 1986; Hara et al., 1987). Commercially available N-acetylneuraminic acid (Neu5Ac) and N-glycolylneuraminic acid (Neu5Gc) (Sigma, St Louis, Mo.) were used as standards (FIG. 5A).

Figures 5A, 5B, 5C, 5D:
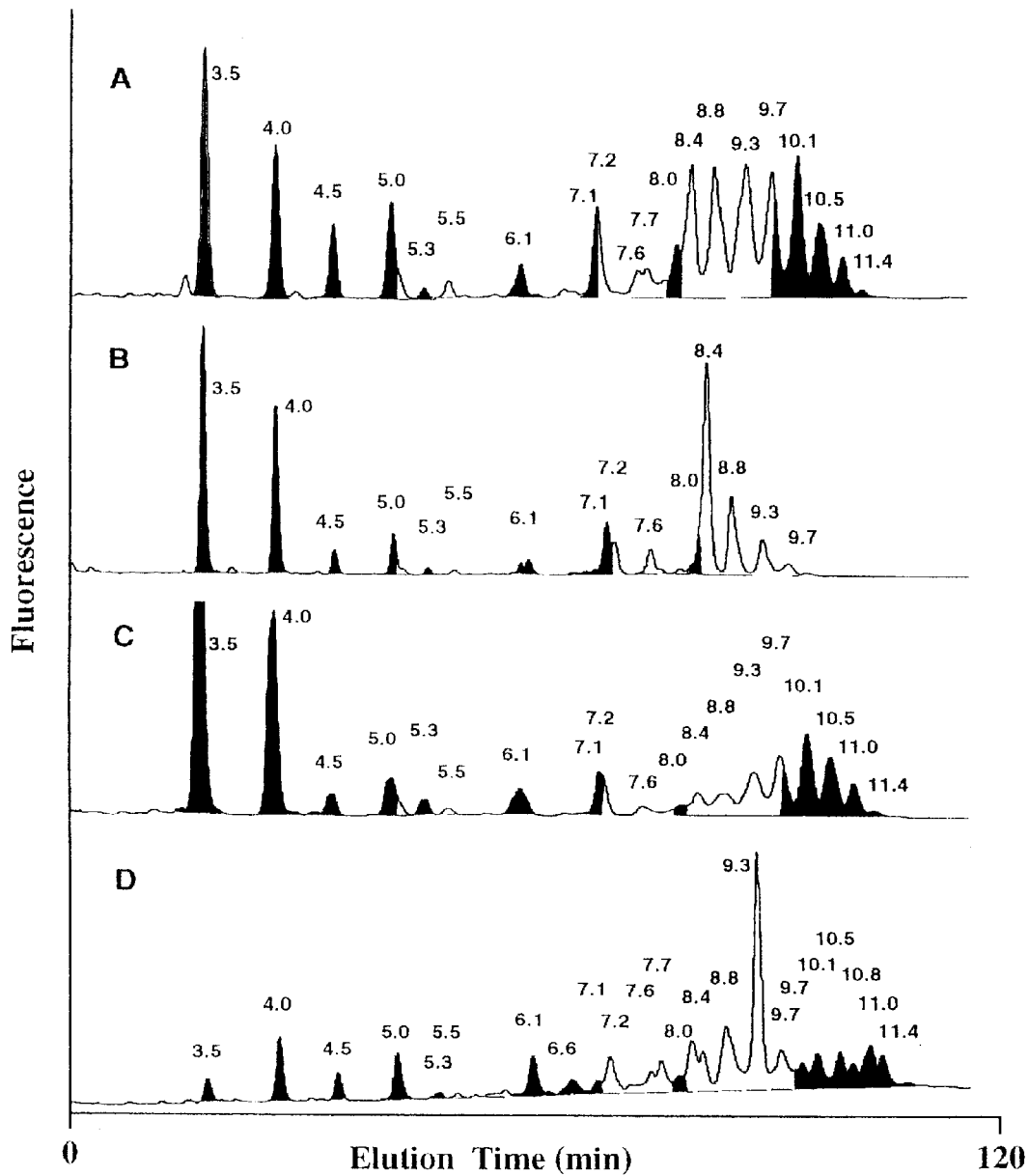
FIGS. 5A, 5B, 5C and 5D show reverse-phase HPLC fractionation of DMB-derivatized sialic acid residues. The DMB-derivatized sialic acids, N-glycolylneuraminic acid (Neu5Gc) and N-acetylneuraminic acid (New5Ac) standards (panel 5A), derivatized sialic acid from SEAP produced in human placental cells (panel 5B) and derivatized sialic acid from SEAP produced in Tn-4h insect tissue culture cells cultured under conditions of microgravity (panel 5C) and normal gravity (panel 5D).

As expected the sialic acid residues attached to the SEAP glycans produced in human placenta were exclusively Neu5Ac (FIG. 5B). The sialic acid residues attached by Tn-4h cells cultured in HARV bioreactors were approximately 94% Neu5Ac, 3% Neu5Gc, and 3% of an unknown α-keto acid (the fastest eluting peak) (FIG. 5C). When equivalent amounts of SEAP produced in T-flasks were similarly analyzed, a barely detectable peak (<3% area of HARV samples) at the elution time of Neu5Ac was reproducibly observed (FIG. 5D) and may represent a previously undetected minor sialylated glycan fraction. The DMB-sialic acid data verified the neuraminidase digestion data.

Because the expression of hundreds of genes are reported to be altered under conditions of microgravity (Hammond et al., 1999; Kaysen et al., 1999), it was considered that the appearance of sialylation of SEAP glycans under conditions of microgravity might have occurred through a decrease in sialidase activity and/or an increase in sialyltransferase activities. However, when the level of sialidase activity was determined using 4-methylumbelliferyl-N-acetylneuraminic acid as a substrate (Sagawa et al.; 1990; Cattaneo et al., 1997), cells grown in T-flasks and HARV bioreactors both contained approximately 0.2 mU (units) of sialidase activity/ μg total cellular protein. Using the standard sialyltransferase assay methodology (Wang et al., 1989; Zhang et al., 1998), sialyltransferase activity was not detected in extracts from cells cultured under either growth condition. This is consistent with previous investigations that were unable to detect sialyltransferase activity in insect cells (Lopez, et al., 1999; Hooker, et al., 1999). It is hypothesized that either the sialyltransferase activity levels in insect cells are too low for detection by current methodology, or that the mammalian-based sialyltransferase assay conditions may be suboptimal for insect sialyltransferases.

Since substrate levels can affect sialylation, it was hypothesized that the microgravity-mediated sialylation might have resulted from an increase in substrate availability. To examine this possibility, we supplemented the medium of cells in T-flasks with 5 mM N-acetylmannosamine (ManNAc), a direct precursor of CMP-sialic acid, that has been shown to increase sialylation in mammalian (CHO) cells (Keppler, et al., 1999; Alfrey et al., 1996). Using ManNAc-supplemented medium and culturing in stationary T-flasks, five sialylated SEAP glycans were identified (FIG. 4C and Table 2) that were structurally identical to the sialylated glycans obtained from cells grown in HARV bioreactors in unsupplemented medium (FIG. 4A and Table 2). These data are consistent with the suggestion that the microgravity culture conditions caused an increase in the Golgi CMP-sialic acid pool, resulting in increased levels of sialylated glycans. This hypothesis was investigated further by comparing the concentration of sialic acid in cells grown in T-flasks and in HARV bioreactors. Using a highly sensitive colorimetric assay (Prozyme, San Leandro, Calif.), it was determined that baculovirus infected Tn-4h cells exhibited higher levels of total sialic acids than uninfected cells (Table 3). The addition of ManNAc to the culture medium increased the levels of sialic acid in uninfected cells but not infected cells. Although there was high variability in sialic acid content of cells grown in HARV bioreactors, the data suggest that microgravity may increase the synthesis of sialic acids in uninfected and infected insect cells. However, it is not clear from these data if the microgravity-mediated sialylation resulted from increased levels of available sialic acid substrates.

TABLE 3

Measurement of Total Cellular Sialic Acid in Tn-4h Insect Tissue Culture Cells

| Culture Condition | nMoles Sialic Acid per mg Cell Protein Culture | |
|---|---|---|
| | Uninfected | Infected |
| T-flask | 46 ± 5 | 92 ± 7 |
| T-flask plus ManNAc | 62 ± 7 | 98 ± 9 |
| HARV | 95 ± 25 | 130 ± 39 |

Use of the Technology

Since the development of the baculovirus expression vector system in the early 1980s, the BEVS has been shown to have a high potential for the commercial production of recombinant proteins. The recombinant, pharmaceutical protein industry is expected to reach $8 billion within the next 5 years. Hundreds of recombinant proteins have been expressed with the BEVS because of the high production levels, ease of purification and the recognition of higher eukaryotic co- and post-translational signal sequences by insect cells. By providing a novel method for increasing the complex glycosylation levels in the BEVS, this invention has the potential to make BEVS even more desirable for industrial protein preparations.

The present disclosure adds to the basic understanding of the effects of microgravity on the biochemical and cellular factors and processes involved in viral replication, protein synthesis and co- and post-translational processing events (glycosylation and secretion). It may provide a great service to the recombinant protein industry and serve as a model for further studies at the organismal level.

The proposed invention may identify novel alterations in protein production, secretion and/or glycosylation. If so, further studies in space may be of great value. Clearly, if microgravity alters DNA virus replication, it may be useful to use this model as a means of determining the potential of novel host: virus interactions in space.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of expressing a recombinant nucleic acid in an insect cell line, using a baculovirus expression system, such that said recombinant nucleic acid being expressed in said baculovirus expression system codes for a protein with N-linked glycosylation, comprising the steps of:

a) culturing cells for use in said baculovirus expression system;

b) infecting said cells with a recombinant baculovirus that expresses said recombinant nucleic acid encoding a recombinant protein that would normally have N-linked glycosylation if expressed in the source organism of said recombinant nucleic acid; and c) culturing said infected cells in media supplemented with serum and dexamethasone or N-acetylmannosamine, such that said recombinant protein is expressed.

2. The method of claim 1 wherein said cells are from the BTI-Tn-5B1-4 cell line or a sub-clone of the BTI-Tn-5B1-4 cell line.

3. A cell culture comprising cells engineered to express a recombinant glycoprotein having terminal sialic acid residues, according to the method of claim 1, and further comprising media supplemented with serum and dexamethasone or N-acetylmannosamine.

4. The method of claim 2 wherein said sub-clone is a cell line designated as BTI-Tn-5B1-4h (4H) and is characterized by its ability to sialylate foreign proteins, when cultured in media supplemented with dexamethasone or N-acetylmannosamine.

5. A method of expressing a recombinant nucleic acid in an insect cell line, using a baculovirus expression system, such that said recombinant nucleic acid being expressed in said baculovirus expression system codes for a protein with N-linked glycosylation, comprising the steps of:

a) culturing cells for use in said baculovirus expression system;

b) infecting said cells with a recombinant baculovirus that expresses said recombinant nucleic acid encoding a recombinant protein that would normally have N-linked glycosylation oligosaccharides with terminal sialic acid residues, if expressed in the source organism of said recombinant nucleic acid; and c) culturing said infected cells in media supplemented with serum and dexamethasone or N-acetylmannosamine, such that said recombinant protein with N-linked glycosylation is expressed and obtains oligosaccharides having terminal sialic acid residues.

6. The method of claim 5, wherein said cells are from the BTI-Tn-5B1-4 cell line or a sub-clone of the BTI-Tn-5B1-4 cell line.

7. A cell culture comprising cells engineered to express a recombinant glycoprotein having terminal sialic acid residues, according to the method of claim 5, and further comprising media supplemented with serum and dexamethasone or N-acetylmannosamine.

8. The method of claim 6, wherein said sub-clone is a cell line designated as BTI-Tn-5B1-4h (4H) and is characterized by its ability to sialylate foreign proteins.

9. A method of culturing insect cells comprising the steps of:

a) culturing insect cells in a medium that includes serum; and b) supplementing said medium with dexamethasone or N-acetylmannosamine, such that N-acetylglucosaminyl-transferase or galactosyl-transferase activities are induced.

10. The method of claim 9 wherein said insect cells are from a cell line selected from the group consisting of Sf21, BTI-Tn-5B1-4 and BTI-Tn-5B1-4h.

11. A method of culturing insect cells comprising the steps of:

culturing insect cells in a medium that includes serum and dexamethasone or N-acetylmannosamine, such that N-acetylglucosaminyl-transferase, galactosyl-transferase or sialic acid transferase activities are induced.

12. A cell line designated BTI-Tn-5B1-4h, characterized in that N-acetylglucosaminyl-transferase, galactosyl-transferase or sialic acid transferase activities are induced, when said cell line is cultured in a medium that includes serum and is supplemented with dexamethasone or N-acetylmannosamine.

13. A cell line having all the distinguishing characteristics of a cell line designated BTI-Tn-5B1-4h.

* * * * *